US012064167B2

(12) United States Patent
Teng et al.

(10) Patent No.: US 12,064,167 B2
(45) Date of Patent: Aug. 20, 2024

(54) METHOD OF TREATING OR ALLEVIATING ERECTILE DYSFUNCTION

(71) Applicants: Gaojun Teng, Nanjing (CN); Yonghua Dong, Shanghai (CN); Huaqing Yin, Shanghai (CN); Qi Zhang, Nanjing (CN); Meijun Shen, Shanghai (CN); Jiulin Guo, Shanghai (CN)

(72) Inventors: Gaojun Teng, Nanjing (CN); Yonghua Dong, Shanghai (CN); Huaqing Yin, Shanghai (CN); Qi Zhang, Nanjing (CN); Meijun Shen, Shanghai (CN); Jiulin Guo, Shanghai (CN)

(73) Assignee: Shanghai Golden Leaf Medtech Co., Ltd., Shanghai (CN)

( * ) Notice: Subject to any disclaimer, the term of this patent is extended or adjusted under 35 U.S.C. 154(b) by 390 days.

(21) Appl. No.: 16/574,039

(22) Filed: Sep. 17, 2019

(65) Prior Publication Data

US 2020/0008871 A1    Jan. 9, 2020

Related U.S. Application Data

(63) Continuation-in-part of application No. 16/147,789, filed on Sep. 30, 2018, now abandoned, which is a
(Continued)

(30) Foreign Application Priority Data

Aug. 5, 2014  (CN) .......................... 201410381377.6
Oct. 17, 2014  (CN) .......................... 201410554508.6
Aug. 27, 2019  (CN) .......................... 201910798477.1

(51) Int. Cl.
| A61B 18/14 | (2006.01) |
| A61N 1/05  | (2006.01) |
| A61N 1/40  | (2006.01) |
| A61B 18/00 | (2006.01) |
| A61M 25/00 | (2006.01) |

(52) U.S. Cl.
CPC ............ *A61B 18/1492* (2013.01); *A61N 1/05* (2013.01); *A61N 1/403* (2013.01);
(Continued)

(58) Field of Classification Search
CPC ...... A61B 18/1492; A61B 2018/00083; A61B 2018/00267; A61B 2018/00434;
(Continued)

(56) References Cited

U.S. PATENT DOCUMENTS 6,006,755 A * 12/1999 Edwards .............. A61B 18/148
                                                            606/41
6,602,248 B1 * 8/2003 Sharps ............... A61B 18/1402
                                                            606/32
(Continued)

*Primary Examiner* — Eun Hwa Kim
*Assistant Examiner* — C. C. P
(74) *Attorney, Agent, or Firm* — George Guosheng Wang; Upstream Research and Patent LLC

(57) ABSTRACT

The present invention provides a method of treating or alleviating erectile dysfunction in a patient. Multiple electrodes are placed within a segment of the internal iliac artery of the patient and against blood vessel wall of the internal iliac artery. Radiofrequency energy is released through at least one of the multiple electrodes to nearby tissues, so as to increase the temperature of the nearby tissues and induce a thermal alteration of the nearby tissues.

17 Claims, 28 Drawing Sheets

Related U.S. Application Data continuation-in-part of application No. 15/501,662, filed as application No. PCT/CN2015/081584 on Jun. 16, 2015, now abandoned.

(52) U.S. Cl.
CPC .............. *A61B 2018/00083* (2013.01); *A61B 2018/00267* (2013.01); *A61B 2018/00434* (2013.01); *A61B 2018/00577* (2013.01); *A61B 2018/00678* (2013.01); *A61B 2018/00821* (2013.01); *A61B 2018/1467* (2013.01); *A61M 2025/0036* (2013.01)

(58) Field of Classification Search
CPC ........... A61B 2018/00577; A61B 2018/00678; A61B 2018/00821; A61B 2018/1467; A61N 1/05; A61N 1/403; A61M 2025/0036
See application file for complete search history.

(56) References Cited

U.S. PATENT DOCUMENTS

| | | | | |
|---|---|---|---|---|
| 2006/0106298 | A1* | 5/2006 | Ahmed | A61B 18/1492 606/41 |
| 2010/0041943 | A1* | 2/2010 | Hovland | A61F 5/41 600/38 |
| 2011/0130755 | A1* | 6/2011 | Bhushan | A61B 18/14 606/35 |
| 2012/0029500 | A1* | 2/2012 | Jenson | A61B 18/1492 606/33 |
| 2012/0101413 | A1* | 4/2012 | Beetel | A61B 18/1492 601/3 |
| 2012/0271140 | A1* | 10/2012 | Kordis | A61B 5/283 600/375 |
| 2014/0005658 | A1* | 1/2014 | Rosenbegr | A61B 18/14 606/33 |
| 2015/0088112 | A1* | 3/2015 | Barman | A61B 18/1492 606/21 |

* cited by examiner (S1/E1)

(S1/E2)

(S1/E5)

(S1/E6)

(S2/E1)

(S2/E2)

(S2/E3)

(S2/E4)

(S2/E5)

(S2/E6)

(Before Treatment)

(After Treatment)

METHOD OF TREATING OR ALLEVIATING ERECTILE DYSFUNCTION

FIELD OF THE INVENTION

The present invention generally relates to a method of treating or alleviating erectile dysfunction in male patients. More particularly, multiple electrodes are placed within a segment of the internal iliac artery of the patient and against blood vessel wall thereof, and then radiofrequency energy is released through the multiple electrodes to nearby tissues, so as to increase the temperature of the nearby tissues and induce a thermal alteration of the nearby tissues.

BACKGROUND OF THE INVENTION

Erectile dysfunction (ED) is a man's inability to achieve or maintain an erection suitable for satisfactory sex. When a healthy man is sexually aroused, nerves and chemicals work together to relax smooth muscle tissue and widen arteries so that the penis can fill with blood. Veins constrict to keep the blood inside the penis, forming the erection. This blood gives the penis the firmness it needs for sex. Once the man ejaculates, the blood is released back into the body.

ED can happen for many reasons, both physical and psychological, among which poor blood flow to the penis is one of the most common causes. The arteries might not widen enough for sufficient blood to flow in. Or, the veins might not constrict enough to keep the blood from flowing out. Both situations can lead to weak erections. Poor blood flow can be the result of diabetes, heart disease, high cholesterol, and high blood pressure.

Oral medications that can increase blood flow to the penis includes phosphodiesterase type 5 (PDE5) inhibitors like Sildenafil (Viagra), Vardenafil (Levitra, Staxyn), Tadalafil (Cialis), and Avanafil (Stendra). These drugs work by relaxing smooth muscle tissue in the penis, allowing more blood to flow in when a man is sexually stimulated. However, these drugs should not be used by men who take nitrates. Patients with slow drug absorption (e.g., Parkinsonian patients) may need to wait 2-3 hours for an erection to develop after taking PDE5 inhibitors.

Advantageously, the present invention provides a method, as an alternative of or in addition to the PDE5 inhibition, for treating or alleviating erectile dysfunction in a patient.

SUMMARY OF THE INVENTION

In various exemplary embodiments, the method includes at least the steps of:
(1) placing multiple electrodes within a segment of an internal iliac artery of the patient and against blood vessel wall of the internal iliac artery by percutaneous transluminal intravascular access;
(2) adhering a surface electrode on an external surface such as skin of the patient; and
(3) releasing radiofrequency energy through at least one of the multiple electrodes to nearby tissues, so as to increase the temperature of the nearby tissues and induce a thermal alteration of the nearby tissues.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

Figure 1A:
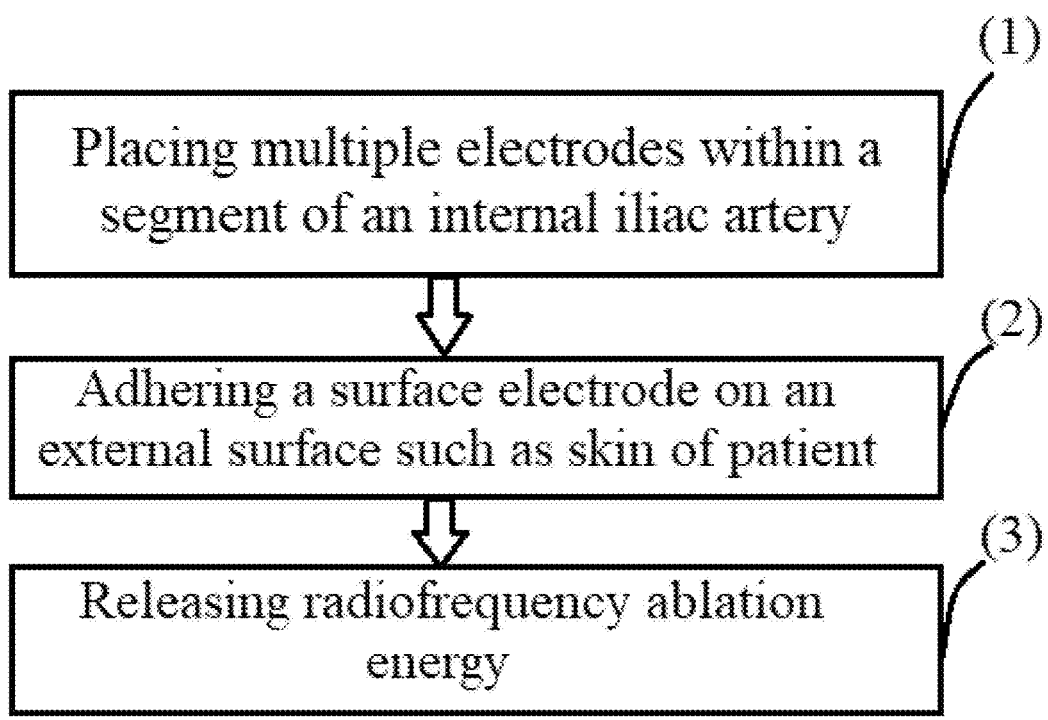
FIG. 1A is a flow chart of the method according in an exemplary embodiment of the present invention.
Figure 1B:
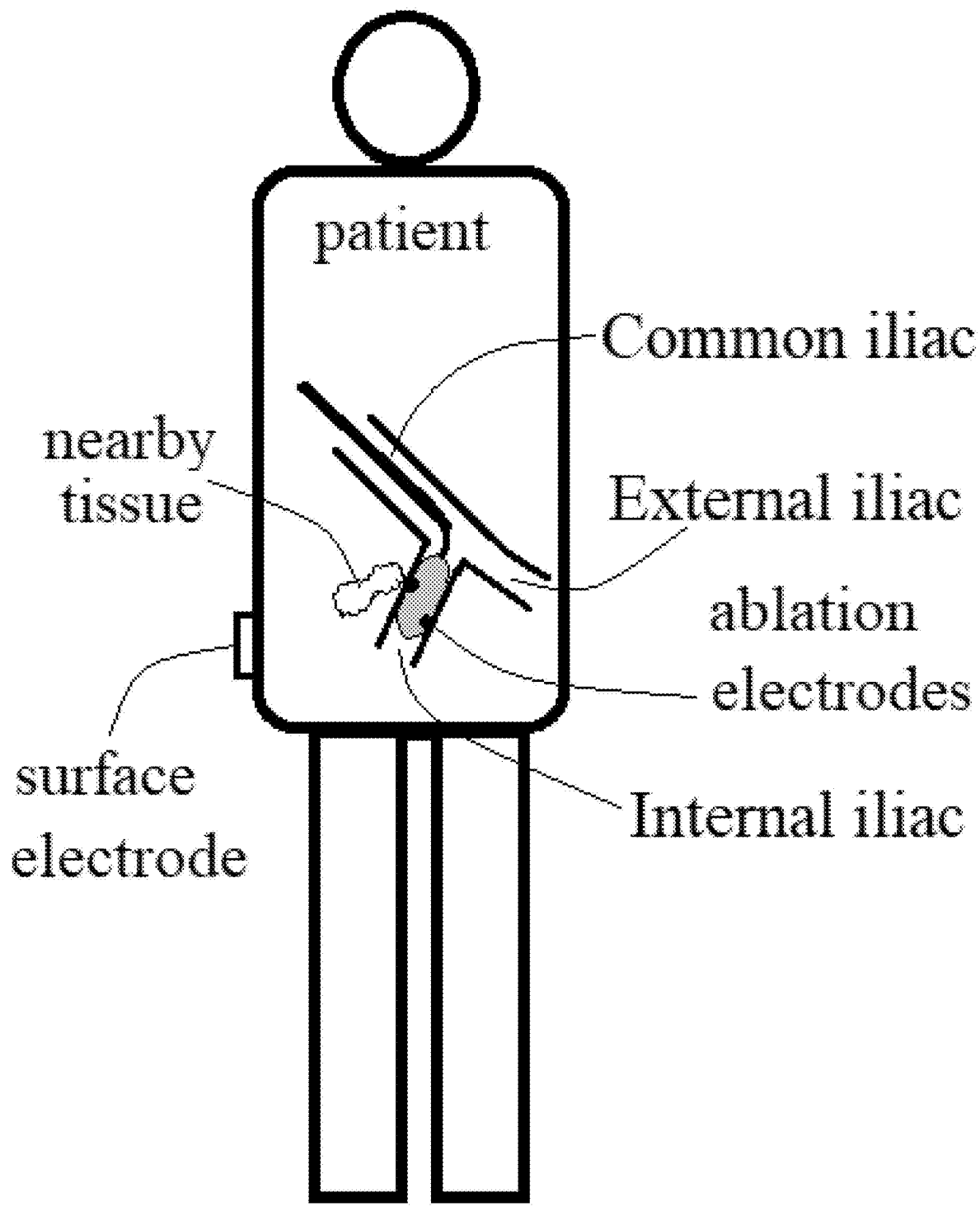
FIG. 1B illustrates the target segment in the internal iliac artery of a patient in an exemplary embodiment of the present invention.

As shown in FIGS. 1A and 1B, the present invention provides a method of treating or alleviating erectile dysfunction (ED) in a patient. Step (1) is placing multiple radiofrequency ablation electrodes (internal electrodes) within a segment of an internal iliac artery of the patient and against blood vessel wall of the internal iliac artery by percutaneous transluminal intravascular access. In preferred embodiments, such segment starts from the junction of the internal iliac artery and the common iliac artery, i.e. a beginning portion of the internal iliac artery. There may be 1~12 internal electrodes such as 6 radiofrequency (RF) electrodes with the segment.

Various embodiments of the present invention use the femoral artery for the endovascular method. Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort. Femoral puncture also allows access to virtually all of the arterial territories and affords favorable ergonomics for the operator in most instances.

In step (2), a surface electrode (or external electrode) is adhered on an external surface such as skin of the patient. The method may further include a step of adjusting or changing the adhesion position of the surface electrode on the back or butt of the patient (not on the belly of the patient) to vary the impedance between the surface electrode and a given electrode within the internal iliac artery until the impedance falls within the range of 200-320, preferably 250-300 Ohms, before step (2).

In Step (3), the radiofrequency energy may be released at a level of no more than 9 W (joule per second) to prevent spasm of the patient. The inventors have unexpectedly discovered that an energy level of higher than 9 W has a risk of spasm. The radiofrequency energy may be released through an alternating current of 460-470 KHz such as 465 KHz between the surface electrode and a given electrode within the internal iliac artery.

In Step (3), the radiofrequency energy may be released with a temperature threshold setting of 60° C. to ensure that collagen does not denature, tissue does not shrink, and cell wall does not break, in the nearby tissue. In general, when tissue temperature rises above about 50° C., protein is permanently damaged. If heated over about 65° C., collagen denatures and tissue shrinks. If heated over about 65° C. and up to 100° C., cell walls break and oil separates from water. If heated above ~100° C., tissue desiccates.

The thermal heating effects according to the present invention can include both thermal ablation and non-ablative thermal alteration or damage (e.g., via sustained heating and/or resistive heating). Desired thermal heating effects may include raising the temperature of the target segment above a desired threshold to achieve non-ablative thermal alteration, and/or above a higher temperature to achieve ablative thermal alteration. For example, the target temperature can be above body temperature (e.g., approximately 37° C.) but less than about 45° C. for non-ablative thermal alteration, or the target temperature can be about 45-60° C. or higher for the ablative thermal alteration. The time period for non-ablative thermal alteration (<45° C.) is defined as Tna, the time period for ablative thermal alteration (≥45° C.) is defined as Ta, and the ratio between the two is defined as Rna/a.

In step (3), the radiofrequency energy may be released for a continuous period of 60-180 such as 120 seconds for each of the multiple electrodes one by one, which protocol is defined as one session. Step (3) may include one, two, three, four, or more such sessions that are separately carried out. The thermal alteration comprises non-ablative thermal alteration, ablative thermal alteration, or any combination thereof; and wherein the thermal alteration produces a lesion with a depth of 5-8 mm or 5.9-6.9 mm such as about 6.4 mm in the nearby tissues. In various embodiments, as described above, the time period for non-ablative thermal alteration (<45° C.) is defined as Tna, the time period for ablative thermal alteration (≥45° C.) is defined as Ta, and the ratio between the two is defined as Rna/a; and Rna/a is generally in the range of from 4:116 to 72:48 (seconds). For example, Rna/a within a session for a patient may be selected from 4:116, 5:115, 6:114, 7:113, 8:112, 9:111, 10:110, 11:109, 12:108, 13:107, 15:105, 16:104, 17:103, 18:102, 19:101, 20:100, 25:95, 30:90, 72:48, or any combination thereof.

According to some embodiments of the invention, an external control unit can be coupled to a catheter to provide RF energy and temperature monitoring. An electrode activation circuitry may be configured to control activation and deactivation of the multiple electrodes in accordance with a predetermined energy delivery protocol and in response to signals received from temperature measuring circuitry.

According to some embodiments, temperature at or near the electrode and/or electrode-tissue interface can be measured using an optical fiber that extends along the catheter shaft and terminates at or near the electrode assembly. In some configurations, temperature measurements can be made by an optical fiber that has evanescent loss that varies with temperature, or by analyzing the Raman scattering of the optical fiber.

Temperature sensors provide for continuous monitoring of tissue temperatures, and RF generator power is automatically adjusted so that the target temperatures are achieved and maintained. An impedance sensor arrangement may be used to measure and monitor electrical impedance during the process, and the power and timing of the RF generator may be moderated based on the impedance measurements or a combination of impedance and temperature measurements.

Temperature-measurement devices are for example, thermocouples, thermistors, and other temperature sensors. Following types of thermocouples may be used in the present invention: nickel alloy, platinum/rhodium alloy, tungsten/rhenium alloy, gold/iron alloy, noble metal alloy, platinum/molybdenum alloy, iridium/rhodium alloy, pure noble metal, Type K, Type T, Type E, Type J, Type M, Type N, Type B, Type R, Type S, Type C, Type D, Type G, and/or Type P.

According to some embodiments, impedance can be measured and monitored for each electrode, in a unipolar configuration, or between electrode assemblies, in a bipolar configuration. Changes in tissue impedance due to heating and ablation can be monitored by an external control unit, alone or along with temperature monitoring, to enable automatic or semi-automatic control of an ablation procedure.

Without being bound to any particular theory, it is believed that the process of the present invention causes controllable injury to nerves in the neighborhood of the target internal iliac artery. The nerves may include those within the walls of the internal iliac artery, and one or more blood vessels branching off from the internal iliac artery. The nerves also include those unassociated with any walls of blood vessels. The "controllable injury" according to the present invention includes a spectrum of nerve injuries: (1) transient and reversible nerve injury, (2) more severe than (1) but remain reversible nerve injury if the process of the invention is terminated in a timely manner; and (3) severe and irreversible nerve injury, resulting in permanent cessation of nerve activity.

As used herein, the terms "distal" and "proximal" define a position or direction with respect to the treating clinician or clinician's control device (e.g., a handle assembly). "Distal" or "distally" refers to a position distant from or in a direction away from the clinician or clinician's control device. "Proximal" or "proximally" refers a position near or in a direction toward the clinician or clinician's control device.

The present invention provides a method for altering/ablating extravascular target tissue from within a blood vessel, particularly within the patient's internal iliac artery. With the treatment according to the present invention, the extent and relative permanency of nerve injury may be tailored to achieve a desired reduction in sympathetic nerve activity (including a partial or complete block) and to achieve a desired degree of permanency (including temporary or irreversible injury).

In preferred embodiments, the multiple electrodes consist of six electrodes configured to create interrupted spiral, but full circumferential, lesions on internal wall of said segment of the internal iliac artery of the patient. The multiple electrodes used in the present method may be a part of any suitable catheter apparatus, for example, the catheter device as described in Chinese Patent Application 201410035836.5 published as CN 103767787A, the content of which is incorporated herein in its entirety.

Figure 1C:
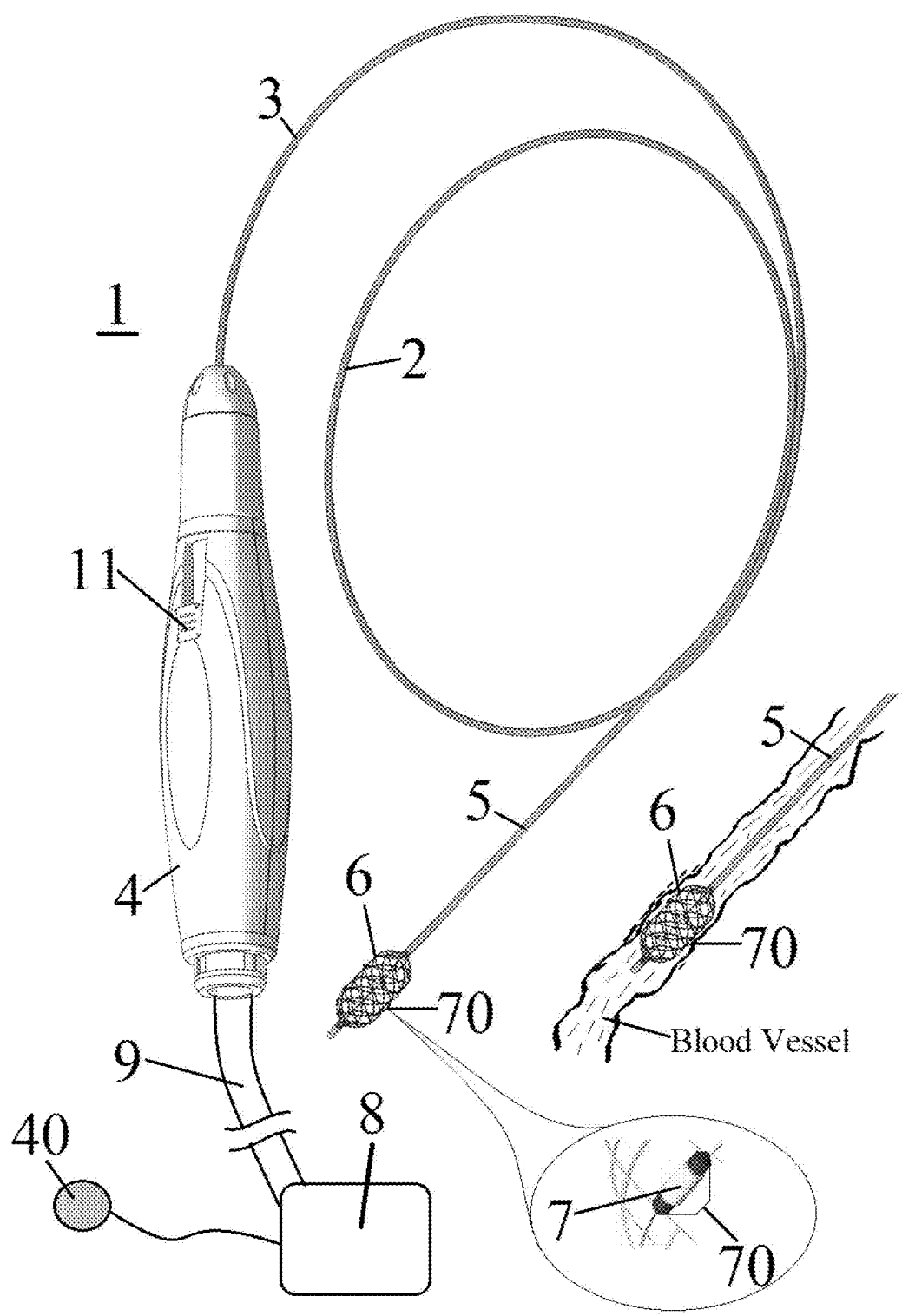
FIG. 1C schematically shows a catheter system used in an exemplary embodiment of the present invention.

In various exemplary embodiments, the multiple electrodes used in the present method are six electrodes in a catheter apparatus as shown in FIG. 1C. The system includes a catheter apparatus 1 that can be operably coupled to an energy source or energy generator 8. The catheter apparatus 1 includes an elongated shaft 2 having a proximal portion 3, a handle assembly 4 at a proximal region of the proximal portion 3, and a distal portion 5 extending distally relative to the proximal portion 3. The catheter apparatus 1 further includes an expandable carrier 6 carrying at least one therapeutic assembly 70 including a therapeutic member 7 for intravascular treatment. The carrier 6 is located at, or proximate to, the distal portion 5 of the elongated shaft 2.

Figure 2:
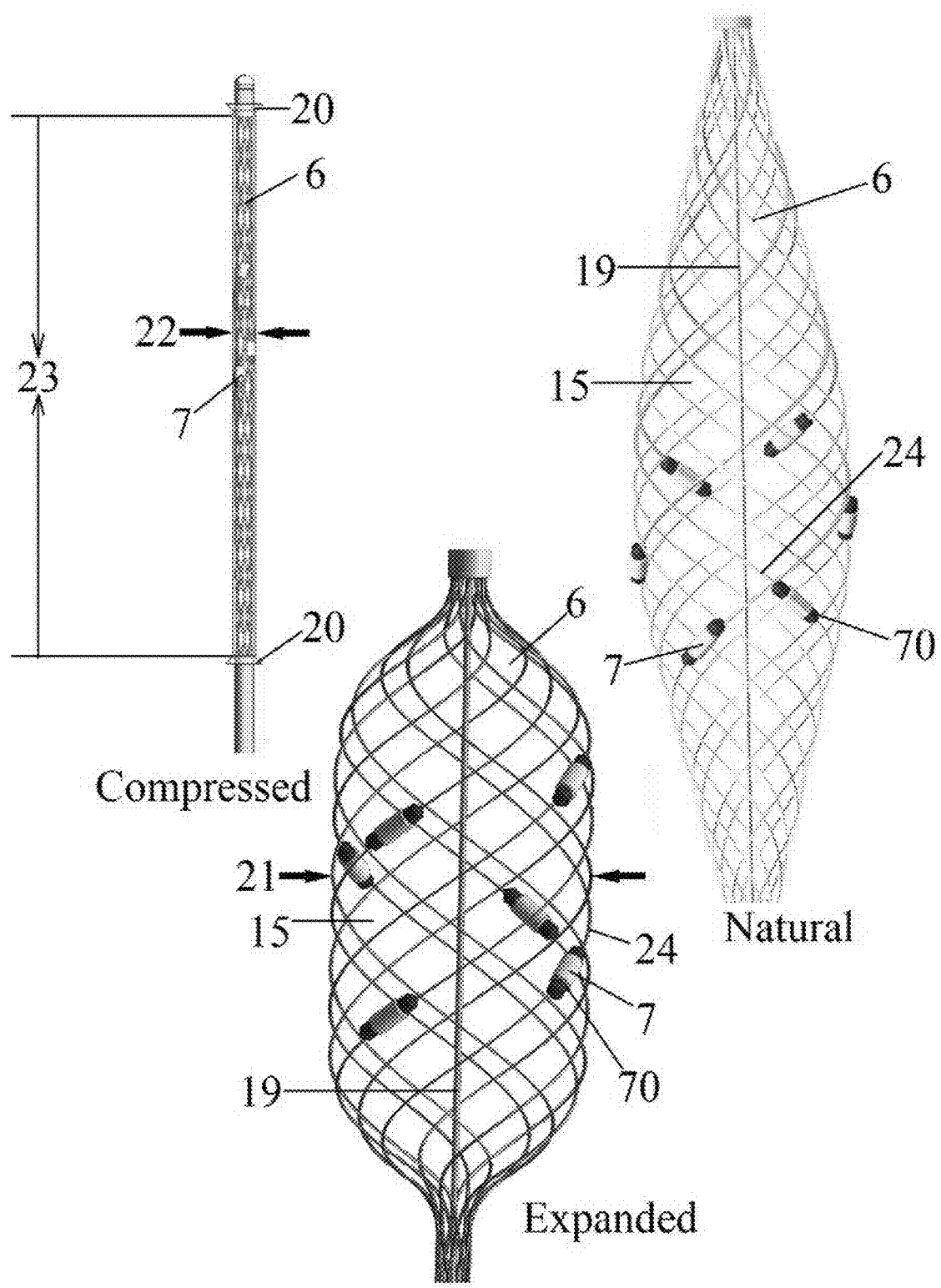
FIG. 2 shows different configurations of the carrier used in an exemplary embodiment.

As shown in FIG. 2, the carrier 6 is configured to be delivered to a blood vessel in a compressed (or low-profile, or delivery, or compacted) configuration. The carrier 6 in compressed configuration can be stored within a protective tube 20. Upon delivery to the target site within the blood vessel, the carrier 6 may be deployed into an expanded (or treatment, or deployed) configuration, bringing the therapeutic member 7 in contact with the walls of the vessel. In various embodiments, therapeutic member 7 is configured to deliver energy at the treatment site and provide therapeutically-effective electrically- and/or thermally-induced medical effect. In some embodiments, the carrier 6 may be placed in the deployed configuration or arrangement via remote actuation, e.g., via an actuator 11, such as a knob, pin, or lever carried by the handle 4, as shown in FIG. 1C. In other embodiments, however, the carrier 6 may be movable between the delivery and deployed configurations using other suitable mechanisms or techniques (e.g., self-expanding). For example, the carrier 6 may be deployed into a natural configuration without any external force imposed upon it, i.e. carrier 6 is neither compressed nor expanded, also bringing the therapeutic member 7 in contact with the walls of the vessel. In some embodiments, a delivery sheath (not shown) is used for deploying the carrier 6. The carrier 6 can self-expand and lengthen when the delivery sheath is retracted.

The carrier 6 is capable of expanding to a maximum diameter 21 that is larger than a collapsed diameter, as shown in FIG. 2. Further, the carrier 6 may be sized so that the maximum diameter 21 is larger than the lumen diameter of the blood vessel. In some embodiments, when inserted into a patient, the carrier 6 expands radially to span the vessel lumen. In other examples, the largest transverse dimension of the carrier 6 is approximately or slightly less than the diameter of the blood vessel lumen, so as to give room to other parts projecting outwardly from the carrier 6. A slight amount of vessel distension may be caused without undue injury and the carrier 6 may expand such that its largest transverse dimension is slightly more than the natural lumen diameter of the blood vessel, or such that the therapeutic member 7 is slightly pressed into the wall of the blood vessel. Sometimes, the carrier 6 that causes slight and non-injurious distension of an artery wall may advantageously provide stable contact force between the therapeutic member 7 and the artery wall and/or hold the therapeutic member 7 in place even as the artery moves with respiratory motion and pulsing blood flow. In some embodiments, the blood vessel lumen diameter can restrict the expansion of the carrier 6 and provide a limit to the maximum diameter 21. This restriction can cause the carrier 6 to form more of a cylindrical tapered shape than a prolate spheroid shape. Because the lumen diameter varies from patient to patient, the carrier 6 may be capable of assuming a range of diameters between the compressed diameter 22 and the maximum diameter 21, as shown in FIG. 2.

The carrier 6 may be characterized by its length 23 along the axis of the elongated shaft 2 or control wire 19. As the carrier 6 expands; its diameter 21 increases and its length 23 decreases. That is, when the carrier 6 expands, its distal end moves axially towards its proximal end. Accordingly, the expanded length 23 is shorter than the unexpanded or natural, or collapsed or compressed, length. In some embodiments, only the proximal end or only the distal end of the carrier 6 is fixedly coupled to the elongated shaft 2. In such a configuration, the distance between the proximal end and the distal end of the carrier 6 changes as the carrier 6 moves between the expanded and collapsed configurations.

The dimensions of the carrier 6 are influenced by its physical characteristics and its configuration (e.g., expanded vs. unexpanded), which in turn may be selected with blood vessel geometry in mind. The expanded configuration length 23 of the carrier 6 is less than the corresponding or counterpart length 23 in the compressed configuration. In some embodiments, the expanded configuration length 23 may be less than about 50%, 55%, 60%, 65%, 70%, 75%, 80%, 85%, or 90% of the corresponding or counterpart compressed length 23. Further, in some embodiments, the expanded configuration diameter 21 may be at least 1.2×, 1.25×, 1.5, 1.75×, 2×, 2.25×, 2.5×, 2.75×3×, 3.25×, 3.5×, 3.75×, 4×, 4.25×, 4.5×, 4.75×, 5×, 10×, 15×, 20×, 30× or 40× of the compressed diameter 22.

The axial length 23 of the carrier 6 may be selected to be no longer than a patient's target blood vessel. A blood vessel may constrict, dilate or move in response to blood flow changes or changes in a patient's breathing, etc. The carrier 6 may be selected to be used in conjunction with a particular blood vessel lumen diameter, taking into account that this lumen diameter may change (e.g., up to 20%) during the time that the carrier 6 is in place. As such, the largest diameter 21 of the carrier 6 may be sufficiently oversized relative to the blood vessel to allow for additional expansion during use. In one embodiment, the largest diameter 21 may be at least 1.2×, 1.5×, or 2× an estimated lumen diameter of the targeted blood vessel. In addition, stable contact with the blood vessel is facilitated by the contact force of the carrier 6 against the blood vessel wall. This contact force is influenced by the materials and construction of the carrier 6. The carrier 6 may be fabricated with super-elastic material such as nickel titanium alloy (nitinol) or composite nitinol with polymer coating for insulation.

Referring to FIGS. 1C and 2, the carrier 6 may carry two or more therapeutic members 7 for intravascular treatment. The therapeutic member 7 may be for example an electrode or a heating element, which is configured to deliver energy such as electrical energy, radiofrequency (RF) electrical energy, pulsed electrical energy, and thermal energy to a target blood vessel after being advanced via a catheter along a percutaneous transluminal path. For example, an energy generator 8 may supply a continuous or pulsed RF electric field to the therapeutic member 7. Although a continuous delivery of RF energy is desirable, the application of RF energy in pulses may allow the application of relatively higher instantaneous power (e.g., higher power), longer or shorter total duration times, and/or better controlled intravascular therapy. Pulsed energy may also allow for the use of a smaller therapeutic member 7.

For example, the purposeful application of energy to tissue by therapeutic member(s) 7 may induce one or more desired thermal heating effects on localized regions of the blood vessel and adjacent regions thereof. The thermal heating effects can include both thermal ablation and non-ablative thermal alteration or damage (e.g., via sustained heating and/or resistive heating). Desired thermal heating effects may include raising the temperature of target tissue above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher (such as 60° C.) for the ablative thermal alteration.

When therapeutic members 7 are employed, they may function, for example deliver power, independently (i.e., may be used in a monopolar fashion), either simultaneously, selectively, or sequentially, and/or may deliver power between any desired combination of the members 7 (i.e., may be used in a bipolar fashion). Furthermore, the doctor optionally may be permitted to choose which therapeutic member(s) 7 are used to function medically, such as power delivery in order to form highly customized lesion(s) within the blood vessel, as desired. For example, an RF electric field causes lesion formation via resistive heating of tissue exposed to the electric field. As will be described in more details, the therapeutic member 7 is mounted or integrated into the carrier 6. As the carrier 6 is expanded, the therapeutic member 7 is placed in contact with the wall of a blood vessel. The carrier 6 ensures the contact force of the therapeutic member 7 does not exceed a maximum force, thus advantageously providing a more consistent contact force that may allow for more consistent lesion formation.

Referring back to FIG. 1C, the energy source or energy generator 8 (e.g., a RF energy generator) may be configured to generate a selected form and magnitude of energy for delivery to the target treatment site via therapeutic member 7. The energy generator 8 can be electrically coupled to the catheter apparatus 1 via a cable 9. A control mechanism (not shown), such as foot pedal, may be connected (e.g., pneumatically connected or electrically connected) to the energy generator 8 to allow the doctor to initiate, terminate and, optionally, adjust various operational characteristics of the energy generator, for example, power delivery. The energy generator 8 can be configured to deliver the treatment energy via an automated control algorithm and/or under the control of the doctor. In addition, the energy generator 8 may include one or more evaluation or feedback algorithms to provide feedback to the doctor before, during, and/or after the intravascular treatment. The generator 8 may be part of a device or monitor that may include processing circuitry, such as a microprocessor. The processing circuitry may be configured to execute stored instructions relating to the control algorithm. The monitor may be configured to communicate with the catheter apparatus 1 to control power to the therapeutic member 7 and/or to obtain signals from the therapeutic member 7 or any associated sensors within or outside the therapeutic assembly 70. The monitor may be configured to provide indications of power levels or sensor data, such as audio, visual or other indications, or may be configured to communicate the information to another device.

In some embodiments, the catheter apparatus 1 may be configured to provide delivery of a monopolar electric field via the therapeutic member 7 (e.g. an electrode). In such embodiments, a skin electrode or surface electrode 40 (as shown in FIG. 1C) may be electrically connected to the energy generator 8 and attached to the exterior of the patient, and may function as a neutral or dispersive electrode during the intravascular treatment.

Figure 3:
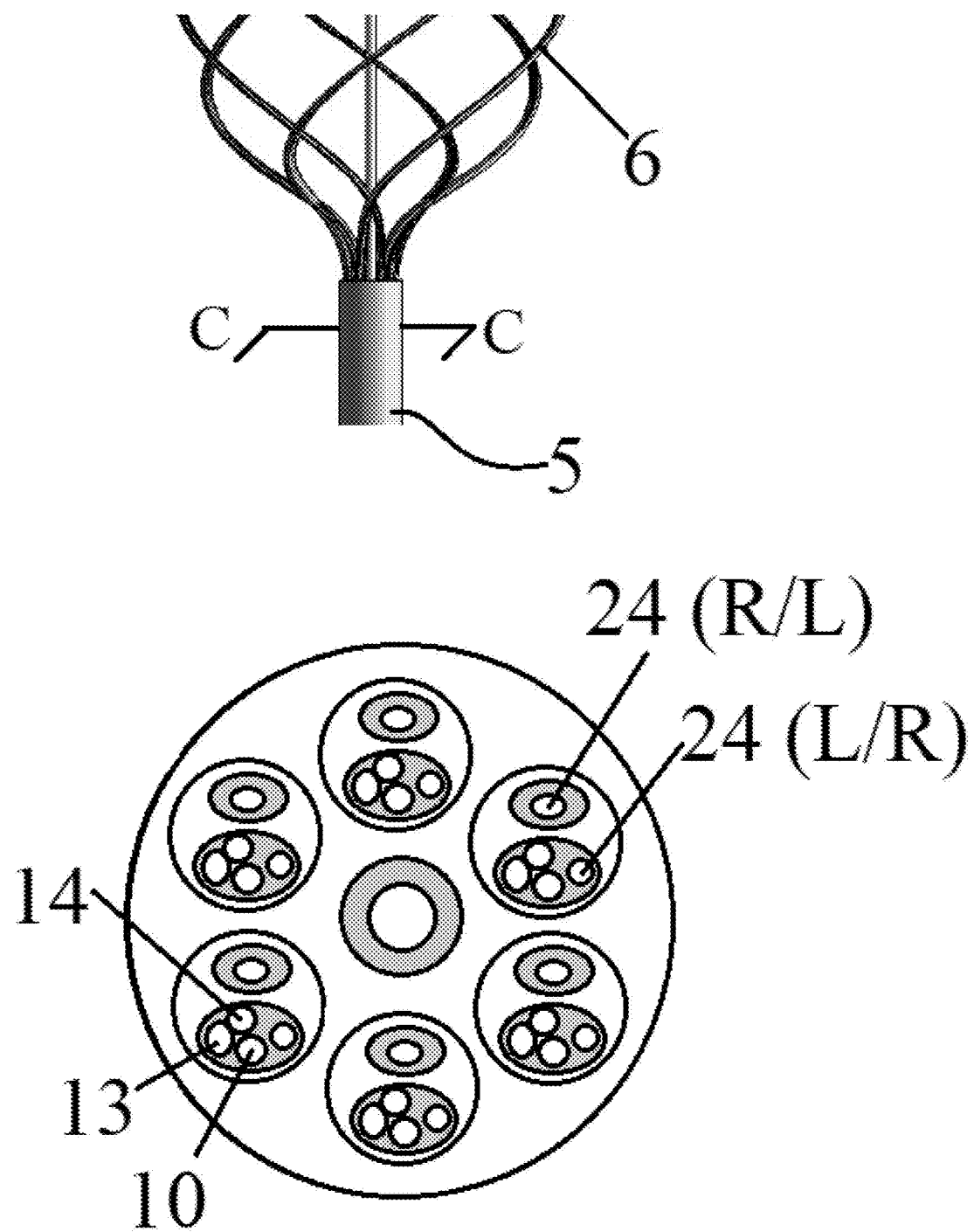
FIG. 3 is a cross-sectional view along C-C of the elongated shaft near the carrier used in an exemplary embodiment.

As shown in FIG. 3, at least one supply wire 10 (such as RF wire 10) passes along the elongated shaft 2 or through a lumen in the elongated shaft 2 to the therapeutic member 7 and transmits the treatment energy from the energy source/generator 8 to the therapeutic member 7.

Figure 4:
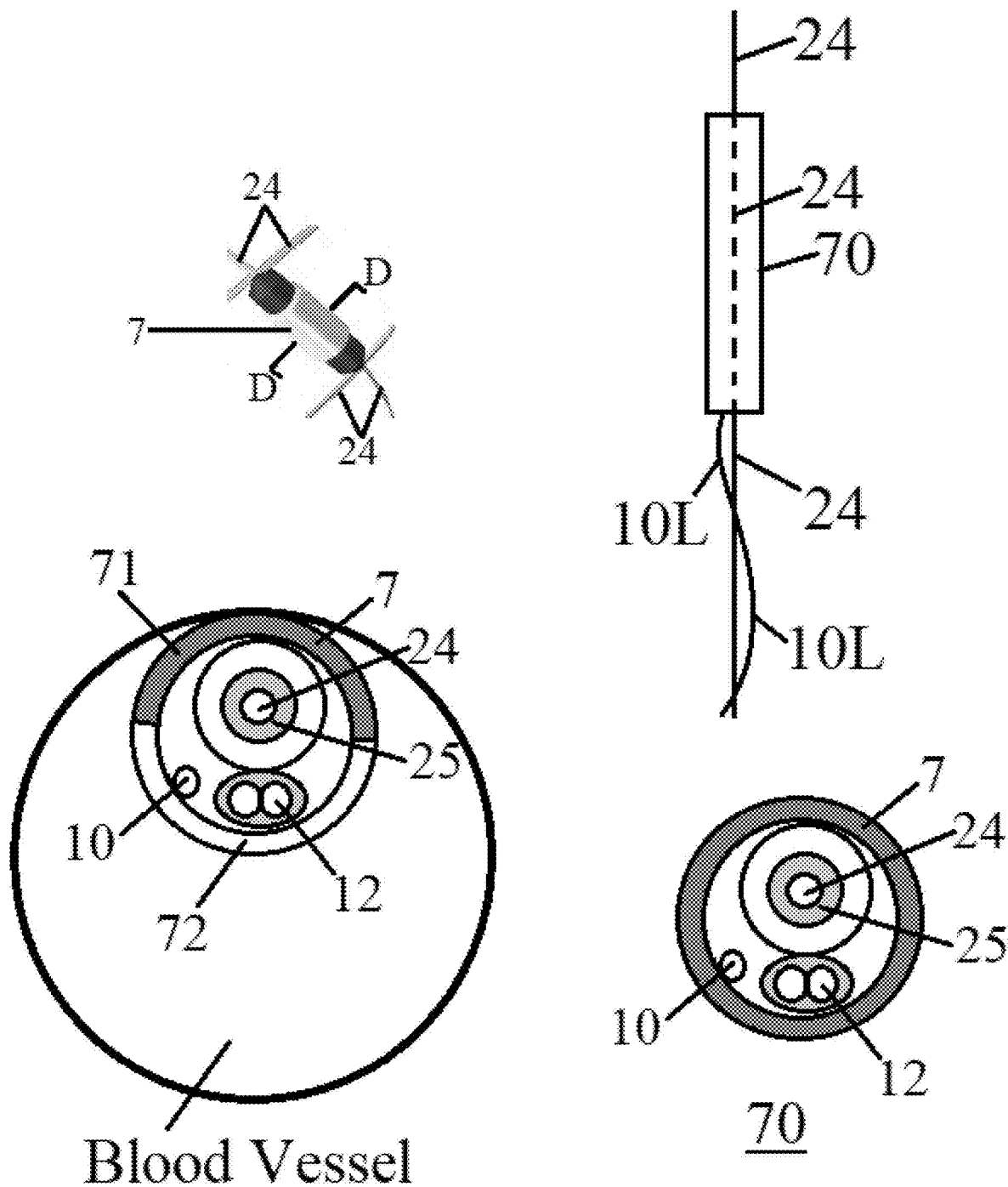
FIG. 4 is a cross-sectional view along D-D of a therapeutic assembly and its position and orientation in a blood vessel.

With reference to FIG. 4, one or more sensors measuring temperature (e.g., thermocouple 12, thermistor, etc.), impedance, pressure, optical, flow, chemical or other parameters, may be located proximate to the therapeutic member 7, e.g. within the therapeutic assembly 70 (i.e. as a part of the therapeutic assembly 70), or not within the therapeutic assembly 70 (i.e. not a part of the therapeutic assembly 70). For example, a total of two supply wires such as thermocouple wires 13 and 14 as shown in FIG. 3 may be included, in which both wires 13 and 14 could transmit the signal from the sensor such as the thermocouple 12, and one wire 13 or 14 could serve dual purpose and also convey RF energy to the therapeutic member 7 (e.g. a RF electrode) without a separate RF wire 10. Alternatively, both wires 13 and 14 could transmit energy to the therapeutic member 7 (e.g. a RF electrode) without a separate RF wire 10.

In various embodiments, energy delivery may be controlled and monitored via data collected with the sensor(s), such as temperature sensors (e.g., thermocouples, thermistors, etc.), impedance sensors, pressure sensors, optical sensors, flow sensors, chemical sensors, etc., which may be incorporated into or on the therapeutic member 7, e.g. within the therapeutic assembly 70, the carrier 6, and/or in/on adjacent areas on the distal portion 5. A sensor may be incorporated into the therapeutic assembly 70 with the therapeutic member 7 in a manner that specifies whether the sensor(s) are in contact with tissue at the treatment site and/or are facing blood flow. It is important to specify temperature sensor placement relative to tissue and blood flow, since a temperature gradient across the electrode from the side facing blood flow to the side in contact with the vessel wall may be up to about 15° C. (for platinum-iridium electrodes). For gold electrodes, this temperature gradient can be around, for example, 1-2° C. In some embodiments, the temperature gradient can vary based, at least in part, on the electrode configuration/material. Significant gradients across the electrode in other sensed data (e.g., flow, pressure, impedance, etc.) can also take place.

The sensor(s) may, for example, be incorporated on or near the side of the therapeutic member 7 that contacts the vessel wall at the treatment site during power and energy delivery or may be incorporated otherwise, such as on the opposing side of the therapeutic member 7 that faces blood flow during energy delivery, and/or may be incorporated within any suitable regions of the therapeutic member 7 (e.g., distal, proximal, quadrants, etc.). In some embodiments, multiple sensors may be provided at multiple positions along the therapeutic member 7, the therapeutic assembly 70, or carrier 6, and/or relative to blood flow. For example, a plurality of circumferentially and/or longitudinally spaced sensors may be provided. In one embodiment, a first sensor may face the vessel wall during treatment, and a second sensor may face the blood flow.

Additionally or alternatively, various microsensors may be used to acquire data corresponding to the therapeutic member 7, the vessel wall and/or the blood flowing across the therapeutic member 7. For example, arrays of micro thermocouples and/or impedance sensors may be implemented to acquire data along the therapeutic member 7 or other parts of the carrier 6. Sensor data may be acquired or monitored prior to, simultaneous with, or after the delivery of energy or in between pulses of energy. The monitored data may be used in a feedback loop to better control therapy, e.g., to determine whether to continue or stop treatment, and it may facilitate controlled delivery of therapy with an increased or reduced power, or a longer or shorter duration.

When catheter apparatus 1 is being used, the distal portion 5 of the elongated shaft 2 as well as the carrier 6 may be moved through an intravascular path by following a path defined by a guide catheter, a guide wire, or a sheath, such as from a percutaneous access site in the femoral, brachial, radial, or auxiliary artery, to a targeted site within the blood vessel. A section of the proximal portion 3 of the shaft 2 is exposed externally of the patient. By manipulating the proximal portion 3 of the shaft 2 from outside the intravascular path (e.g., via the handle assembly 4), the doctor may advance the shaft 2 through the sometimes tortuous intravascular path and remotely manipulate or actuate the distal portion 5 of the shaft 2. Image guidance, e.g., computed tomography (CT), fluoroscopy, intravascular ultrasound (IVUS), optical coherence tomography (OCT), any other suitable guidance modality, or combinations thereof, may be used to aid the doctor's manipulation. In some embodiments, image guidance components (e.g., IVUS, OCT) may even be incorporated into the catheter apparatus 1 itself. After the carrier 6 is adequately positioned in the blood vessel, it can be expanded or otherwise deployed using the handle 4 or other suitable means until the therapeutic member 7 such as RF electrodes are in stable contact with the inner wall of the blood vessel.

Referring back to FIG. 2, the compressed, collapsed or delivery configuration of the carrier 6 facilitates insertion and/or removal of the catheter apparatus 1 and, in certain embodiments, repositioning of the catheter apparatus 1 within the blood vessel. In the collapsed configuration, the carrier 6 is sized and shaped to fit within the blood vessel and has a diameter that is less than a blood vessel lumen diameter. The carrier 6 is expected to provide stable contact of the therapeutic member 7 with the inner wall of a vessel without occluding the blood flow within the vessel. As the carrier 6 is fabricated or woven from wires, blood can flow through the carrier 6 via interstices 15, the structure of which will be described in more details.

Figure 5:
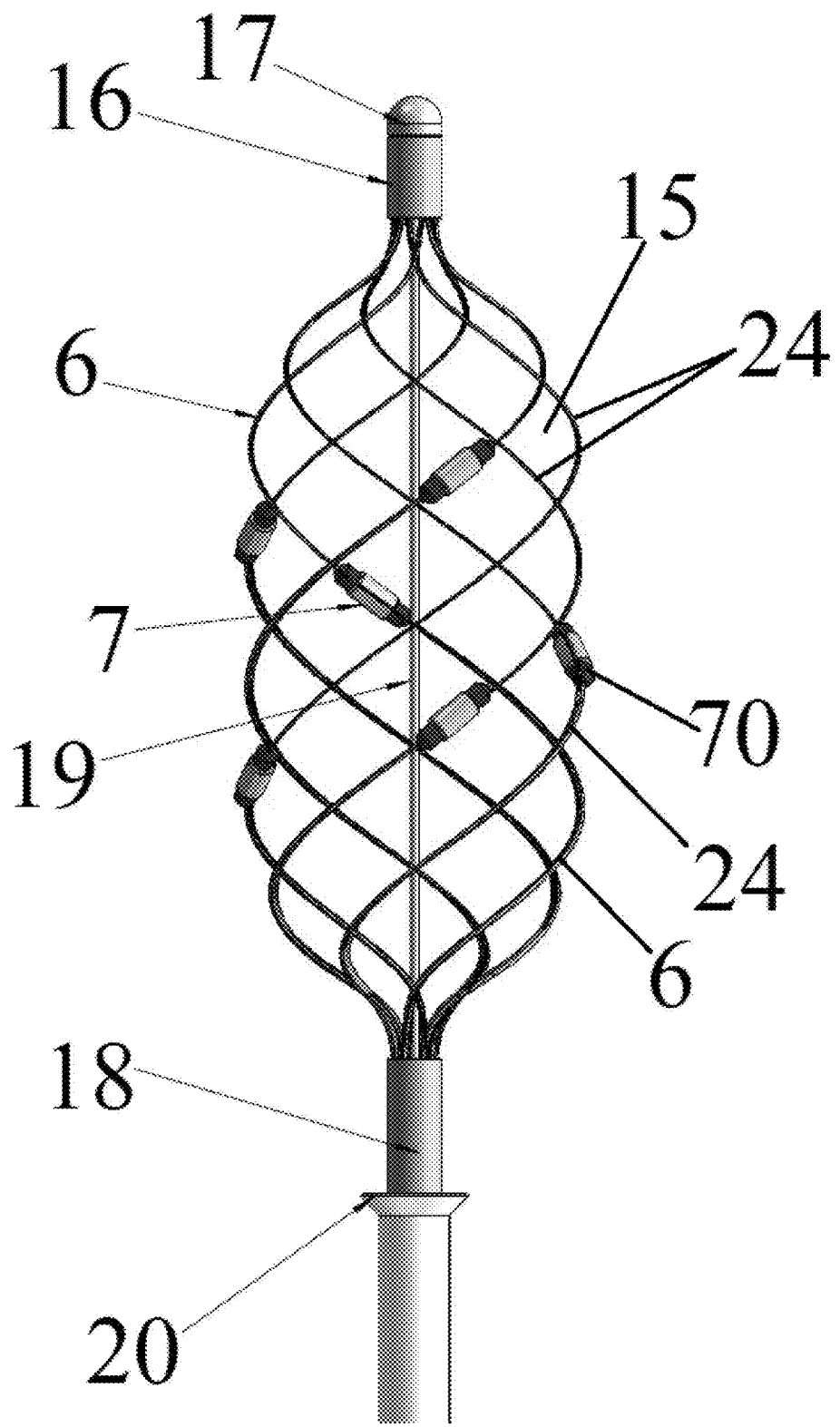
FIG. 5 depicts the specific structure of a carrier used in an exemplary embodiment.

Referring now to FIG. 5, the distal end of the carrier 6 may be coupled to an end piece 16 (e.g., a collar, shaft, or cap) having a rounded distal portion 17 to facilitate atraumatic insertion of the carrier 6 into a blood vessel. Alternatively, a rounded part that is radiopaque (or visible to X-ray imaging such as CT) may replace the rounded distal portion 17 to facilitate atraumatic insertion of the carrier 6 and to track the location of the carrier 6. The proximal end of the carrier 6 may be connected to, or coupled to, the elongated shaft 2 using a multi-lumen coupling 18. Coupling 18, for example, may be an integral end of the elongated shaft 2 (e.g., may not be a separate piece) or may be a separate piece that is associated with the distal region of the elongated shaft 2. The coupling 18 may be formed from the same type of material as the elongated shaft 2, or may be formed from a different material. In one embodiment, the coupling 18 may be formed from a collar, such as a radiopaque band, that surrounds and secures the carrier 6 to an exterior surface of the elongated shaft 2.

The elongated shaft 2, the coupling 18, the carrier 6, and the end piece 16 may include passages sized and shaped to accommodate a control wire or pull/push wire 19 that is fixed to the distal end of the carrier 6 or the end piece 16 and passes through the elongated shaft 2 to the proximal portion 3 of the elongated shaft 2. The control wire 19 facilitates the expansion and/or contraction of the carrier 6 when it is pulled or pushed to shorten or lengthen the carrier 6. For example, pulling (i.e., an increase in tension) the control wire 19 proximally relative to the shaft 2 may trigger expansion of the carrier 6 by drawing end piece 16 closer to coupling 18. Conversely, pushing (i.e., an increase in compression) the control wire 19 distally relative to shaft 2 may lengthen the carrier 6 to a compressed configuration by axially spreading apart end piece 16 and coupling 18. It will be understood that either the shaft 2 or the control wire 19 may be held in fixed position with respect to the patient while the other element is translated to create the relative movements described above. In some embodiments the carrier 6 has elastic or super-elastic shape memory properties such that when force is removed, the carrier 6 elastically returns to a relaxed state or a natural state as shown in FIG. 2. Force may be applied by the control wire 19 to deform the carrier 6 into one state, and when force is removed, the mesh carrier 6 returns to its relaxed state. For example, a relaxed or "natural" state of the carrier 6 may be a half-way expanded configuration as shown in FIG. 2, and the control wire 19 may be pushed to lengthen the carrier 6 and reduce its diameter, placing it in a collapsed or "compressed" configuration as shown in FIG. 2. Alternatively, a relaxed state of the carrier 6 may be a collapsed or compressed configuration and the control wire 19 may be pulled (tension applied) to shorten the carrier 6 and increase its diameter, placing it in an expanded configuration. In some embodiments, the control wire 19 may be a solid or stranded wire or cable made from a metal or polymer. In other embodiments, the control wire 19 may be a hollow tube that can be passed over a guide wire to facilitate insertion through an intravascular path to a targeted site in the blood vessel.

As shown in FIG. 5, the carrier 6 includes structural elements, e.g., wires 24 (or strands, filaments or fibers) arranged to define interstices 15 (or interstitial spaces) therebetween. Because the change in diameter and axial length of the carrier 6 may involve realignment of wires 24 and variations of the geometry of the interstices 15, the makeup of the wires 24 and the geometry of the interstices 15 may at least in part define how much the diameter and length of the carrier 6 change as a result of its configuration changes.

The wires 24 may be formed from biocompatible metals, polymers, or composites. For example, suitable metals can include stainless steel, spring steel, cobalt chromium, gold, platinum, platinum-iridium, stainless steel, or combinations thereof. In one particular embodiment, the carrier 6 may be composed of nitinol with gold plating to enhance radiopacity and/or conductivity. Suitable polymer materials can include, for example, polyethylene terephthalate (PET), polyamide, polyimide, polyethylene block amide copolymer, polypropylene, or polyether ether ketone (PEEK) polymers. In some embodiments, the carrier 6 may be a combination of electrically conductive and nonconductive materials.

In some embodiments, the carrier 6 may be formed at least in part from radiopaque materials that are capable of being imaged fluoroscopically to allow a doctor to determine if the carrier 6 is appropriately placed and/or deployed in the blood vessel. Radiopaque materials may include barium sulfate, bismuth trioxide, bismuth subcarbonate $(BiO)_2CO_3$, powdered tungsten, powdered tantalum, or various formulations of certain metals, including gold and platinum, and these materials may be directly incorporated into the wires 24 or may form a partial or complete coating of the carrier 6.

The carrier 6 may be designed to apply a desired outward radial force to a blood vessel wall when inserted and expanded to contact the inner surface of the wall. The radial force may be selected to avoid injury from stretching or distending the vessel when the carrier 6 is expanded against the wall within the patient. Radial forces that may avoid injuring the blood vessel yet provide adequate stabilization force may be determined by calculating the radial force exerted on a vessel wall by typical blood pressure. For example, a suitable radial force may be less than about 300 mN/mm (e.g. less than 200 mN/mm). Fibers 24 formed from stiffer materials (e.g. metals) may be thinner relative to fibers 24 formed highly flexible polymers to achieve similar flexibilities and radial force profiles. The outward pressure of the carrier 6 may be assessed in vivo by an associated pressure transducer.

The carrier 6 with more open structures (e.g., bigger interstices 15, or lower material per square inch ratios) may have less radial stiffness and strength than more closed structures (smaller interstices 15, or high material density structures). The thickness of fibers 24 also affects outward pressure, radial strength and stiffness. Certain secondary processes, including heat treating and annealing, may harden or soften the fiber material to affect strength and stiffness. In particular, for shape-memory alloys such as nitinol, these secondary processes may be varied to give the same starting material different final properties. For example, the elastic range or softness may be increased to impart improved flexibility. The secondary processing of shape memory alloys influences the transition temperature, i.e., the temperature at which the structure exhibits a desired radial strength and stiffness. This temperature may be set at normal body temperature (e.g. 37° C.).

The carrier 6 may be braided, knit, or woven to form a conformable structure (e.g., a tubular, barrel-shaped, parachute-shaped, or spherical structure) through which fluids may pass. In embodiments, the carrier 6 may include 4-48 fibers. It should be understood that fiber 24 may be formed from a single filament (monofilament) or by a plurality of filaments twisted or otherwise grouped together to form a multifilar fiber. In addition, the carrier 6 may be characterized by its braid pitch, which may be between 1-10 picks (i.e., windings) along its axial length. In preferred embodiments, the carrier 6 may be helically braided with right-handed helix wires and left-handed helix wires) into a generally ovoid, tubular, barrel, or other shaped structure.

In some embodiments, the carrier 6 may be generally symmetrical and coaxial with respect to the elongated shaft 2 or control wire 19. However, it is also contemplated that the carrier 6 may conform to any irregularities in the blood vessel (e.g. a shape of fortune cookie), which may be assessed by imaging or other techniques. For example, particular sizes and types of carrier 6 may be used in conjunction with a patient's particular anatomic features.

For some patients, it may be desirable to configure the therapeutic member(s) 7 in such a manner that they can create either a single lesion or a pattern of multiple focal lesions that are spaced apart circumferentially and/or axially along the longitudinal axis of the blood vessel. A single focal lesion with desired longitudinal and/or circumferential dimensions, one or more full circumferential lesions, multiple circumferentially spaced focal lesions at a common longitudinal position, spiral-shaped lesions, interrupted spiral lesions, generally linear lesions, and/or multiple longitudinally spaced focal lesions along a line parallel to the axis of the blood vessel alternatively or additionally may be created. In other embodiments, the therapeutic member(s) 7 may be used to create lesions having a variety of other geometric shapes or patterns.

Depending on the size, shape, and number of the therapeutic member(s) 7, the lesions created may be circumferentially spaced around the blood vessel, either in a single transverse plane or the lesions may also be spaced apart longitudinally. In some embodiments, it is desirable for each lesion to cover at least 10% of the vessel circumference. It is also desirable that each lesion be sufficiently deep to penetrate into and beyond the adventitia. However, lesions that are too deep run the risk of interfering with non-target tissue and tissue structures, and therefore a controlled depth of treatment is also desirable.

In general embodiments, the therapeutic member(s) 7 may be circumferentially repositioned relative to the blood vessel during treatment. This angular repositioning may be achieved, for example, by compressing the carrier 6 and rotating the elongated shaft 2 via handle assembly 4. In addition to the angular or circumferential repositioning of the therapeutic member(s) 7, it/they optionally may also be repositioned along the lengthwise or longitudinal dimension of the blood vessel. This longitudinal repositioning may be achieved, for example, by translating the elongated shaft 2 via the handle assembly 4, and may occur before, after, or concurrently with angular repositioning of the therapeutic member(s) 7. Repositioning the therapeutic member(s) 7 in both the longitudinal and angular dimensions places it/them in contact with the interior wall of the blood vessel at a second treatment site. RF Energy may then be delivered via the therapeutic member 7 to form a second focal lesion at this second treatment site. For embodiments in which multiple therapeutic members 7 are associated with the carrier 6, the initial treatment may result in two or more lesions, and repositioning may allow additional lesions to be created. One or more additional focal lesions optionally may be formed via additional repositioning of the carrier. In preferred embodiments, the carrier 6 carries a sufficient number of therapeutic member 7 (e.g. RF electrodes), and it does not have to be selectively repositioned within the blood vessel to provide a number of locations for e.g. RF energy delivery.

In certain embodiments, the lesions created via repositioning of the carrier 6 are circumferentially and longitudinally offset from the initial lesion(s) about the angular and lengthwise dimensions of the blood vessel, respectively. The composite lesion pattern created along the blood vessel by the initial energy application and all subsequent energy applications after any repositioning of the therapeutic member(s) 7 may effectively result in a discontinuous lesion (i.e., it is formed from multiple, longitudinally and angularly spaced treatment sites).

Sometimes, it may be desirable to configure the therapeutic member(s) 7 in such a manner to create a composite lesion pattern, as viewed from a proximal or distal end of the vessel, to extend at least approximately all the way around the circumference of the blood vessel under treatment. In other words, each formed lesion covers an arc of the circumference; and each of the lesions, as viewed from an end of the vessel, abut or overlap adjacent lesions to create a virtually circumferential lesion. The formed lesions defining an actual circumferential lesion lie in a single plane perpendicular to a longitudinal axis of the blood vessel. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions.

For example, a cylindrical carrier 6 having therapeutic members 7 affixed to wires 24 in a helical pattern such that therapeutic members 7 are circumferentially and axially offset from one another. The circumferential offset arcs, or corresponding radial angles, may be selected so that when energy is applied to the blood vessel via therapeutic members 7, a roughly helical lesion pattern is formed therein. Depending on the number and positioning of the therapeutic members 7 selectively mounted on wires 24, a helical lesion pattern with any desired number of turns (e.g. 1, 2, 3 or more) may be formed using only a single RF energy application. In other embodiments, the therapeutic members 7 may have a variety of different arrangements relative to each other (e.g., linear, interrupted helix, continuous helix).

In a non-limiting example, the therapeutic members 7 are configured in such a manner to create a virtually circumferential lesion comprising six lesions created in a single helical pattern along the blood vessel; and each lesion spans an arc extending along at least one sixth (or 60 degree) of the vessel circumference such that the resulting pattern of lesions completely encompasses the vessel circumference, when viewed from an end of the vessel. In other examples, however, a virtually circumferential lesion can comprise a different number of lesions.

The axial distances between axially adjacent therapeutic members 7 may be selected so that the edges of the lesions formed by each individual therapeutic member 7 on the blood vessel wall 55 are either overlapping or non-overlapping. The axial distance may be about 2 mm to about 1 cm. In a particular embodiment, the axial distance may be in the range of about 2 mm to about 5 mm. In another representative embodiment, the axially adjacent therapeutic members 7 may be spaced apart about 10-50 mm.

Therapeutic member(s) 7 may be coupled to leads 10L, which may be e.g. a part of RF wire 10, or electrically connected to RF wire 10. The leads 10L may be separate from the carrier 6, or may be loosely or tightly coupled to, adhered to, wrapped around, or integrated into to the carrier 6 (e.g. around/on/with/to a wire 24) to prevent twisting or kinking of the leads. In particular embodiments, to facilitate the stable contact of the therapeutic member(s) 7 to the blood vessel, the therapeutic assembly 70 may be coupled to carrier 6 by weaving lead(s) into the wires 24 of the mesh or threading leads through interstices in the mesh of carrier 6. At least a part of the therapeutic member(s) 7 is positioned on an exterior surface of carrier 6. The positioning of the therapeutic member(s) 7 on the exterior surface may be associated with a desired lesion pattern. Alternatively, as shown in FIGS. 2 and 5, the therapeutic assembly 70 may be directly coupled to the wire 24. The therapeutic assembly 70 is coupled to wire 24, for example via adhesion or threading a wire 24 through an internal bore 25, as shown in FIG. 4.

The therapeutic member 7 may be in the form of an electrically conductive tube. As shown in FIG. 4, the tube electrode 7 may be wound about (or wrapped around) wire 24. In other words, a wire 24 inserts into and passes through the tube electrode 7. For example, six tube electrodes 7 may form a loose-pitch or tight-pitch "dotted", interrupted or discontinuous helix. Regions of the tube electrode 7 that do not contact the blood vessel wall may contribute to cooling of the electrode. Alternatively, as shown in FIG. 4, only portion 71 of the tube electrode 7 may be electrically conductive with the blood vessel wall tissue. That is, the tube electrode 7 can include insulated portion 72 and uninsulated portion 71 in which the insulation is removed. For example, the flow of blood over the portion 72 (which is not contacting vessel wall) provides conductive and convective cooling of a RF electrode 7, thereby carrying excess thermal energy away from the interface between the vessel wall and electrode 7. Electrode cooling can be alternatively or additionally achieved by injecting or infusing cooling fluids such as saline (e.g., room temperature saline or chilled saline) over the electrode and into the blood stream. It may also be desirable to provide enhanced cooling by inducing additional native blood flow across the carrier 6. For example, techniques may be implemented by the doctor to increase perfusion through the target blood vessel or to the carrier 6. These techniques include positioning partial occlusion elements (e.g., balloons) within upstream vascular bodies such as the aorta, or within a portion of the target blood vessel to improve flow across the carrier 6. Because cooling of the electrode 7 is mediated by blood flow, improved cooling may be achieved by redirecting a faster blood flow into the target blood vessel or into the carrier 6 so that the blood flowing around the electrode 7 is relatively faster. Sometimes, without a proper cooling, resistive heating of the tissue may be too aggressive and not enough excess thermal energy is being carried away, resulting in excessive heat generation and increased potential for stenotic injury, thrombus formation and undesirable lesion size.

The therapeutic member 7 may be sized and configured to contact an internal wall of the blood vessel during the treatment. For example, the therapeutic member 7 may take the form of an electrode sized and configured to apply an electrical field of RF energy from the energy generator 8 to a vessel wall. As described above, the electrode 7 may be operated in a monopolar or unipolar mode. In this arrangement, a return path for the applied RF electric field is established, e.g., by an external dispersive electrode or skin electrode 40 (as shown in FIG. 1), also called an indifferent electrode or neutral electrode. The monopolar application of RF electric field energy serves to ohmically or resistively heat tissue in the vicinity of the electrode 7. The application of the RF electrical field thermally injures tissue. For example, a treatment objective may be to thermally induce neuromodulation (e.g., necrosis, thermal alteration or ablation) in the targeted neural fibers. The thermal injury forms a lesion in the vessel wall. Alternatively, a RF electrical field may be delivered with an oscillating intensity that does not thermally injure the tissue whereby neuromodulation in the targeted nerves is accomplished by electrical modification of the nerve signals.

The term "active surface area" of the electrode 7 is defined as the energy transmitting area of the electrode 7 that may be placed in intimate contact against tissue. Too much contact between the electrode and the vessel wall may create unduly high temperatures at or around the interface between the tissue and the electrode, thereby creating excessive heat generation at this interface. This excessive heat may create a lesion that is circumferentially too large. In some instances, too much contact can also lead to small, shallow lesions. Too little contact between the electrode 7 and the vessel wall may result in superficial heating of the vessel wall, thereby creating a lesion that is too small (e.g., <10% of vessel circumference) and/or too shallow.

Figure 6:
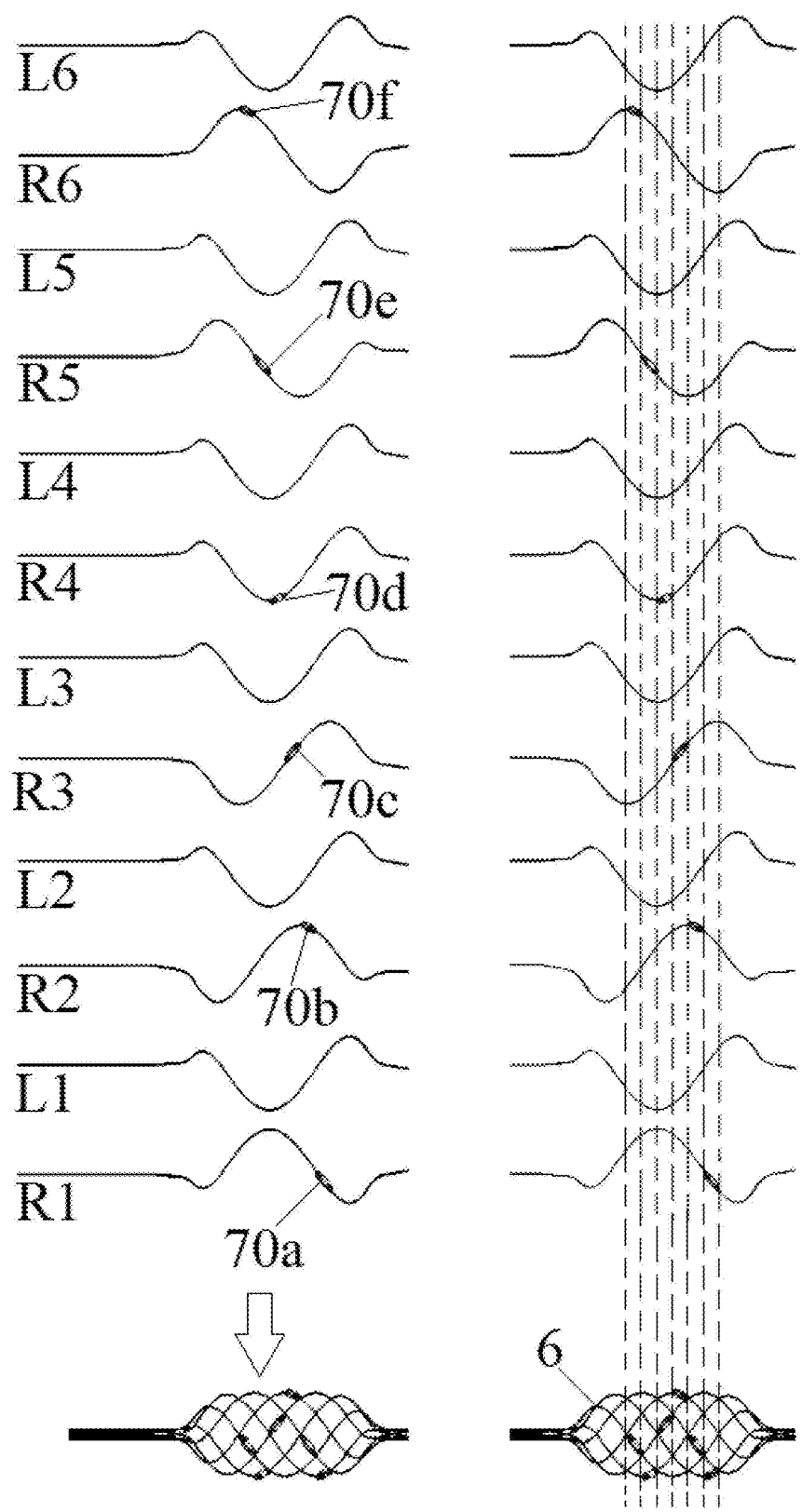
FIG. 6 schematically shows a carrier including right-handed wire helixes and left-handed wire helixes used in an exemplary embodiment.

As described above, the carrier 6 may be helically braided with right-handed helix wires and left-handed helix wires) into a generally ovoid, tubular, barrel, or other shaped structure. In preferred embodiments as shown in FIG. 6, the carrier 6 comprises m (m≥2) right-handed wire helixes such as 6 R-helixes R1~R6 and n (n≥2) left-handed wire helixes such as 6 L-helixes L1~L6. With the line of sight along the helix's axis, if a clockwise screwing motion moves the helix away from the observer, then it is called a right-handed helix; if towards the observer, then it is a left-handed helix. Handedness or chirality (symbolized as R- and L-) is a property of the helix, not of the perspective. A right-handed helix cannot be turned to look like a left-handed one unless it is viewed in a mirror, and vice versa. In some embodiments, the carrier 6 comprises m right-handed wire helixes and n left-handed wire helixes that are plainly or bi-axially woven into a tubular structure, 2≤m≤30 and 2≤n≤30, such as 3≤m≤20 and 3≤n≤20; 4≤m≤15 and 4≤n≤15; 5≤m≤10 and 5≤n≤10. For example, helixes R1~R6 and L1~L6 are plainly or bi-axially woven into carrier 6 with a tubular structure, as shown in FIG. 6.

Figure 7:
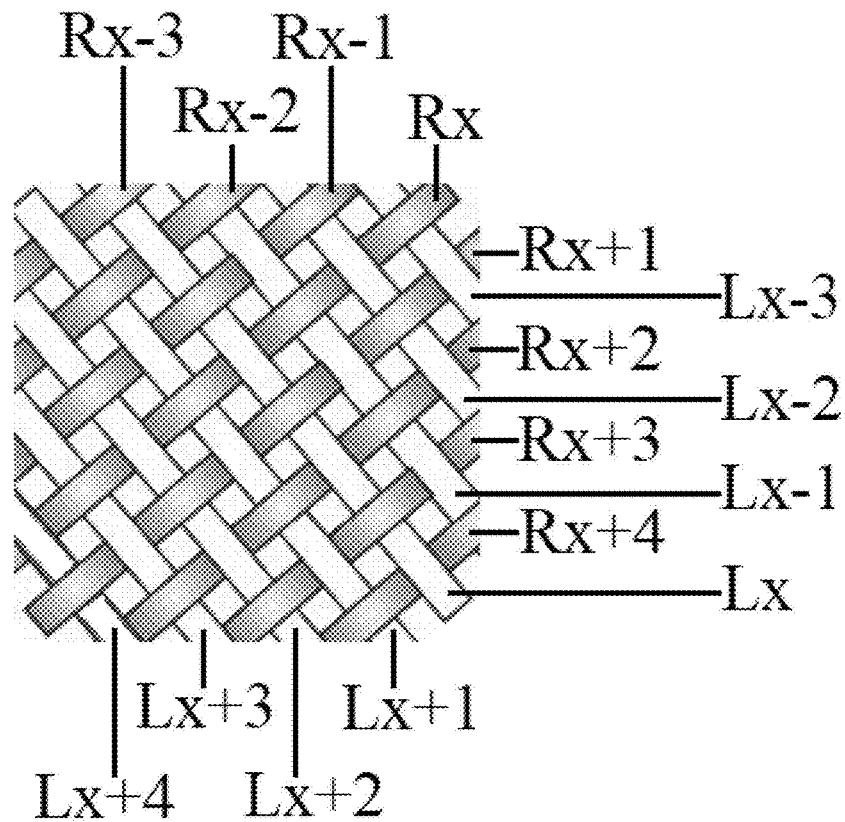
FIG. 7 shows how wires are plainly or bi-axially woven in accordance with an exemplary embodiment of the present invention.
Figure 7:
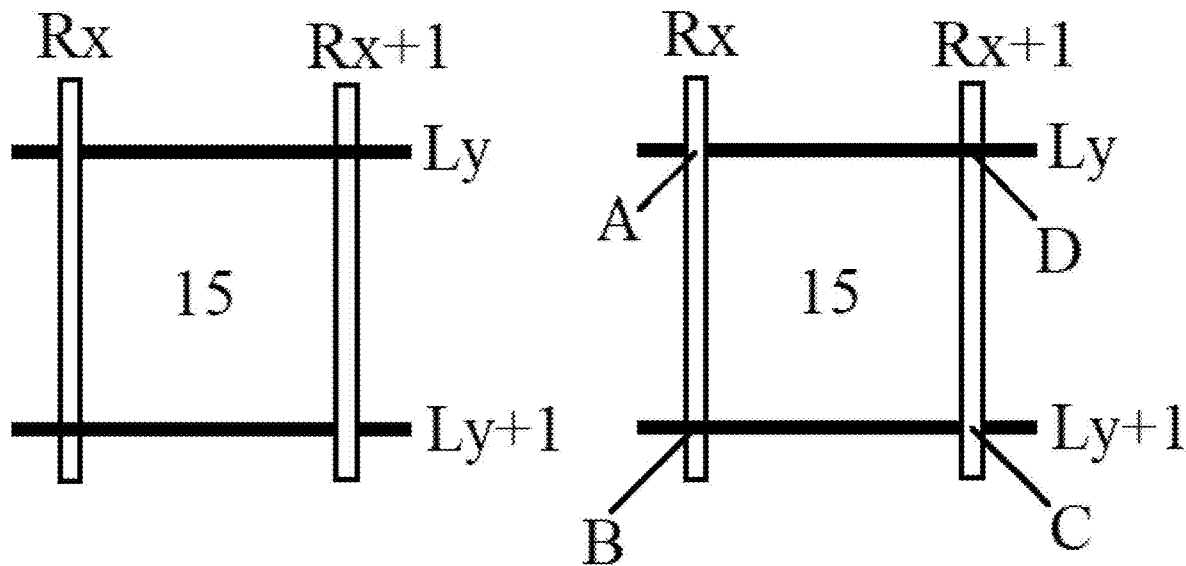

The term "plainly or bi-axially" is defined and explained with reference to FIG. 7. Any right-handed helix wire R (e.g. Rx) is woven into (or between) at least two immediately adjacent left-handed helix wires Ls (e.g. Ly and Ly+1), in such a manner that one L wire (e.g. Ly) is beneath wire R (e.g. Rx), while another L wire which is immediately next to Ly (e.g. Ly+1) is above Rx. In other words, Ly and Ly+1 are located on the opposite sides of wire Rx. A right-handed helix wire Rx+1, that is immediately next to (or adjacent to) wire Rx, is also woven into (or between) two wires Ly and Ly+1, but in an opposite manner to produce an opposite configuration that wire Ly is above wire Rx+1, while wire Ly+1 is beneath Rx+1. By the same token, any left-handed helix wire Ly is woven into at least two immediately adjacent right-handed helix wires Rx and Rx+1, in such a manner that wire Rx is above wire Ly, while wire Rx+1 is below Ly. In other words, Rx and Rx+1 are located on the opposite sides of wire Ly. A left-handed helix wire Ly+1, that is immediately next to (or adjacent to) wire Ly, is woven into two wires Rx and Rx+1, in an opposite manner to produce an opposite configuration that wire Rx is beneath wire Ly+1, while wire Rx+1 is above Ly+1.

In such a pattern, the four wires (Rx, Rx+1, Ly, and Ly+1) will have four intersectional points (or cross-over points) A, B, C and D that are not fixed, and are movable relative to their two corresponding crossed-over wires. For example, point A is moveable relative to wire Rx and/or Ly as wire Rx slides over Ly and/or Ly slides over Rx. Points B, C and D are also moveable for similar reasons and in similar fashions. As a result, the carrier 6 comprises at least one interstice 15 that is defined by four wire helix segments AB, BC, CD and DA selected from two immediately adjacent right-handed wire helixes (Rx and Rx+1) and two immediately adjacent left-handed wire helixes (Ly and Ly+1) that are plainly or bi-axially woven into each other.

Figure 8:
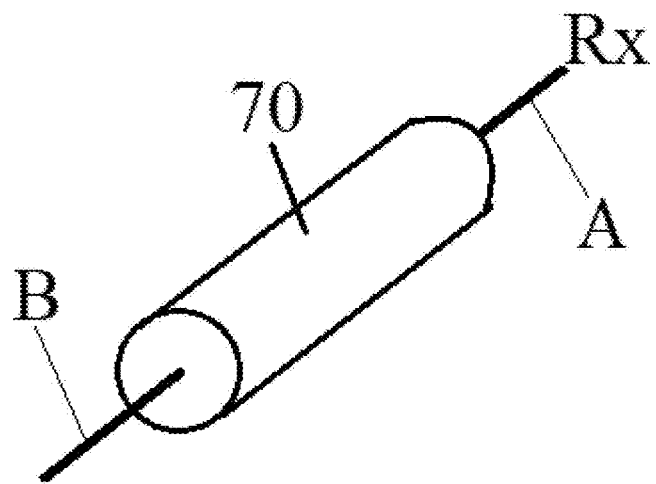
FIG. 8 shows a therapeutic assembly wrapping around a wire helix segment in accordance with an exemplary embodiment.
Figure 8:
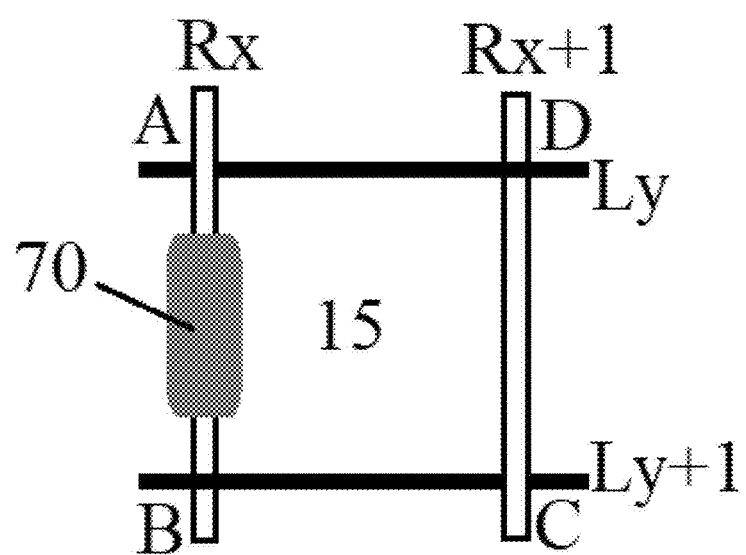

As shown in FIG. 8, at least one therapeutic assembly 70 is configured to wrap around at least one of said four wire helix segments AB, BC, CD and DA (e.g. segment AB) to stabilize said at least one interstice 15. The lengths of helix segments AB, BC, CD and DA vary when the carrier 6's shape is being changed. In some embodiments, only one therapeutic assembly 70 wraps around only one of said four wire helix segments AB, BC, CD and DA (e.g. only segment AB) to stabilize the interstice 15, and does not wrap around any one of the other three helix segments (e.g. segments BC, CD and DA). In a preferred embodiment, therapeutic assembly 70 has a rotational axis (e.g. when it has cylinder shape), and wire helix segment AB penetrates through therapeutic assembly 70 approximately along the rotational axis. By "approximately", it means that the distance between the wire helix segment AB and the rotational axis is always less than 50% of the distance between an edge (or a side surface) of therapeutic assembly 70 and the rotational axis, along any plane perpendicular to the rotational axis. In particularly preferred embodiments, m=n=6, and the carrier 6 carries six therapeutic assemblies 70a-70f as shown in FIG. 6, each of which includes an electrode 7 as the therapeutic member 7, providing six electrodes in total. The six electrodes may be configured to create interrupted spiral but full circumferential lesions on internal wall of a target blood vessel.

Figure 9A:
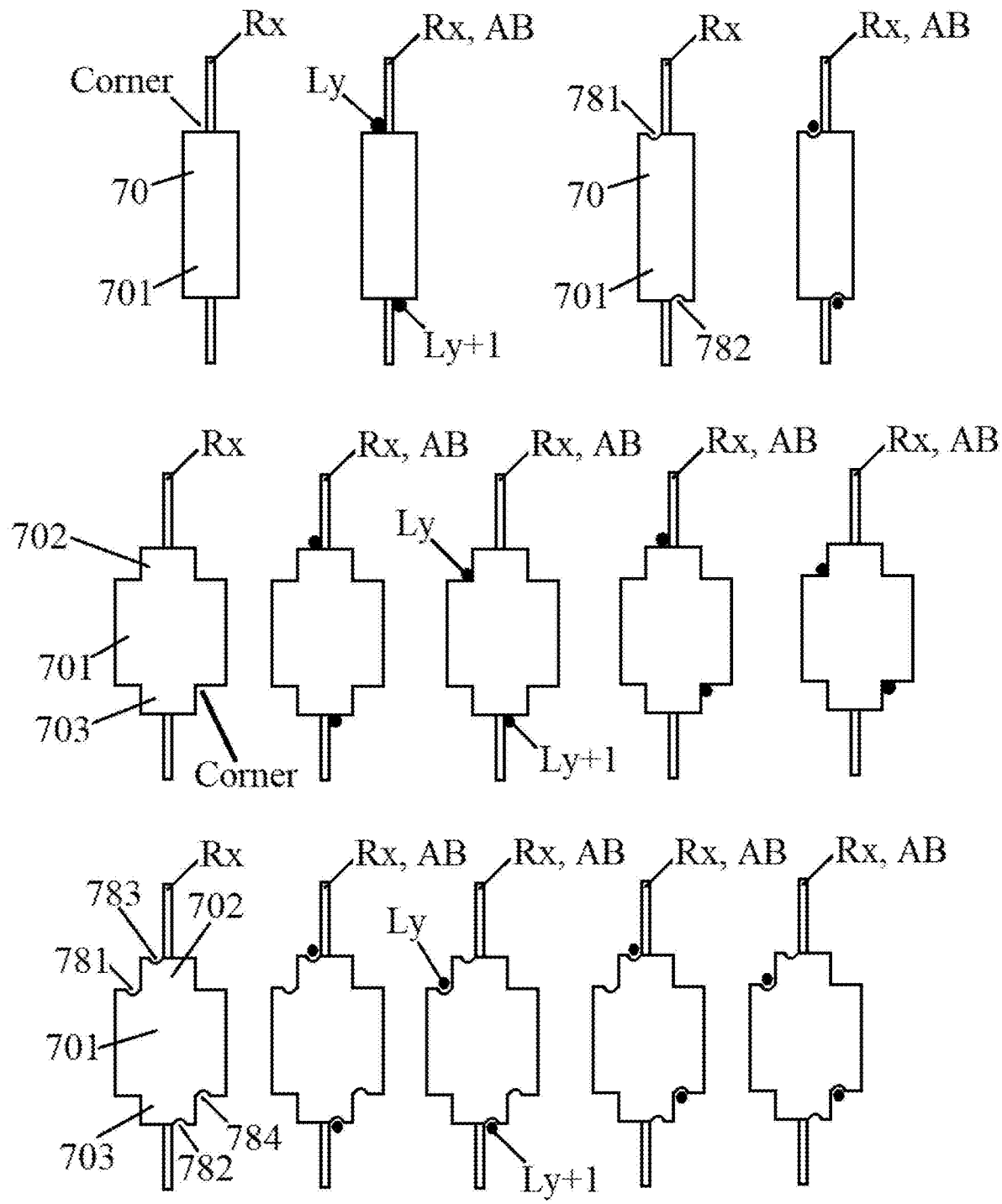
FIG. 9A shows various structures of the therapeutic assembly used in an exemplary embodiment.

As shown in FIG. 9A, the therapeutic assembly 70 may include a main body 701 such as a single cylinder-shaped body 701, without any terminal bodies. Alternatively, assembly 70 may further include two terminal bodies 702 and 703, both of which may be cylinder-shaped, and the main body 701 may be positioned between the two terminal bodies 702 and 703. In other embodiments, terminal bodies 702 and 703 may have a cone shape, tapering down from the main body 701. The cross-sectional area of the main body 701 along a plane perpendicular to the elongation direction of the wire segment AB being wrapped around is larger than cross-sectional areas of both terminal bodies 702 and 703 along a plane perpendicular to the elongation direction of the wire segment AB being wrapped around, which are larger than a cross-sectional area of the wire segment AB itself along a plane perpendicular to the elongation direction of the wire segment AB. The dimension and shape of terminal body 702 may be the same as, or different from, those of terminal body 703.

As shown in FIG. 9A, all the corner areas formed between the main body 701 (when there is no terminal body) and wire Rx, between the main body 701 and terminal body 702 (if present), between the main body 701 and terminal body 703 (if present), between terminal body 702 (if present) and wire Rx, and between terminal body 703 (if present) and wire Rx may be used to accommodate wires Ly and Ly+1, as long as the plainly or bi-axially woven pattern of R- and L-wires is maintained.

At least one of (preferably all) the two terminal bodies 702/703 if any and the main body 710 may include one or more grooves for snugly accommodating or guiding one or more wire helixes that slide(s) over the wire segment around which the therapeutic assembly wraps. For example, body 701/702/703 can be grooved with grooves 781, 782, 783 and 784 near the corner areas for snugly accommodating sliding wires Ly and Ly+1 in a more stable manner, as shown in FIG. 9A. Wires Ly and Ly+1 can slide over wire Rx using the grooves as guides.

Figure 9B:
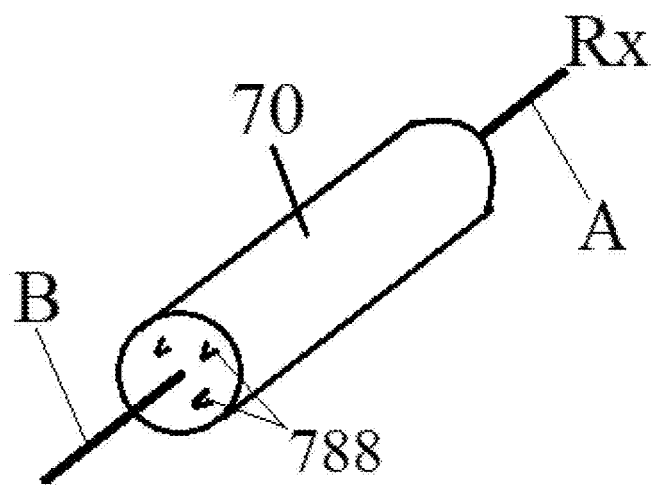
FIG. 9B shows other structures of the therapeutic assembly used in an exemplary embodiment.
Figure 9B:
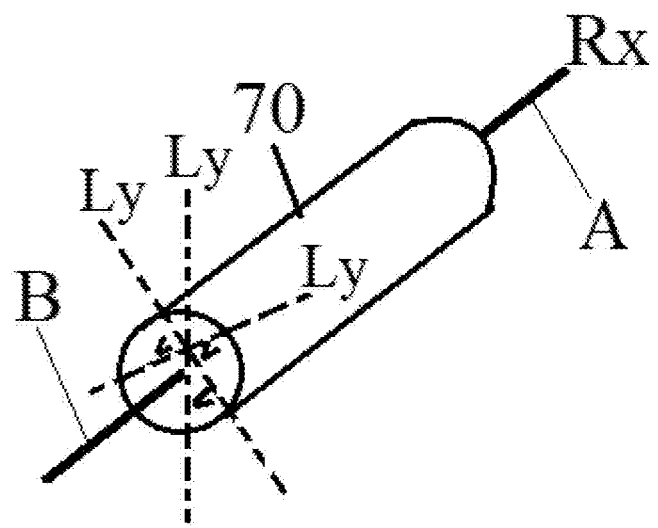

As shown in FIG. 9B, at least one of (preferably all) the two terminal bodies 702/703 if any and the main body 710 may include one, two or more protrusions 788. The gap(s) between segment AB and protrusion(s) 788, and the gap(s) between said protrusion(s) 788 themselves, configured for accommodating or guiding one or more wire helixes Ly or Ly+1 that slide(s) along different directions (represented as the dotted lines Ly) over the wire segment AB around which the therapeutic assembly 70 wraps. When there are three or more protrusions 788, it is preferred that no three protrusions 788 are located along a straight line. As such, we will have as many "Ly guiding directions" as possible.

Figure 10:
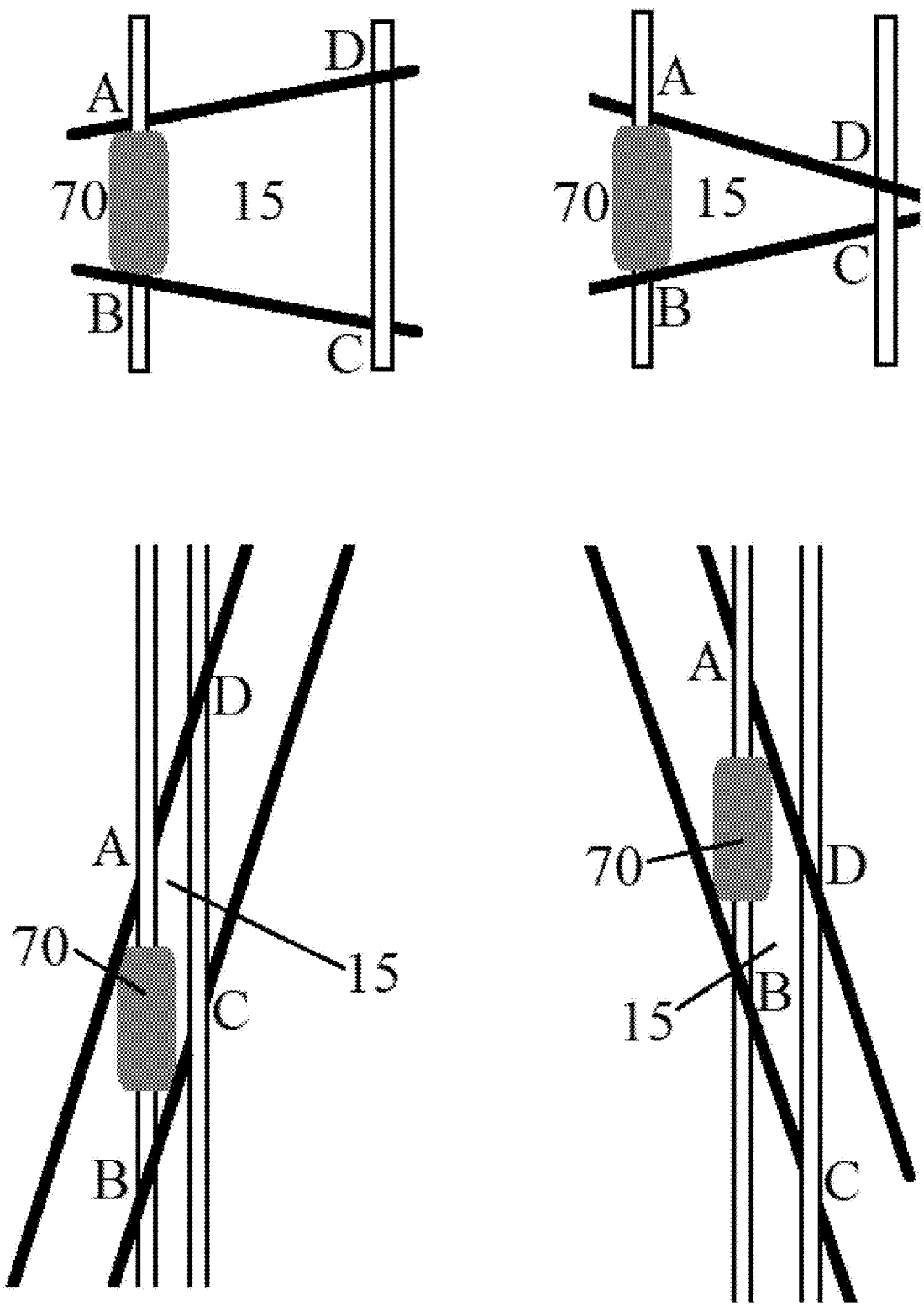
FIG. 10 shows various geometries of the interstice stabilized by a therapeutic assembly in accordance with an exemplary embodiment.

As a result, length of the wire segment AB being wrapped around may be controlled, depending on where wires Ly and Ly+1 sit, to be equal to, or longer than, the main body 701's length along the elongation direction of the wire segment AB, with or without terminal bodies. It may also be controlled to be equal to, or longer than, the main body 701's length combined with the length of only one of the two terminal bodies (702 or 703) along the elongation direction of the wire segment AB. Alternatively, the length of the wire segment AB being wrapped around may be controlled to be equal to, or longer than, the main body 701's length combined with total length of both two terminal bodies (702 and 703) along the elongation direction of the wire segment AB. As such, various minimal lengths of the wire segment AB may be maintained to be greater than a certain positive value when the carrier 6 is being expanded, compressed, or moved along a curved blood vessel, as shown in FIG. 10. With such minimal lengths of the wire segment AB, wires Ly and Ly+1 are prevented from entangling with each other, and the regular shape of the carrier 6 may be quickly recovered after the carrier is seriously bent or distorted.

Figure 11:
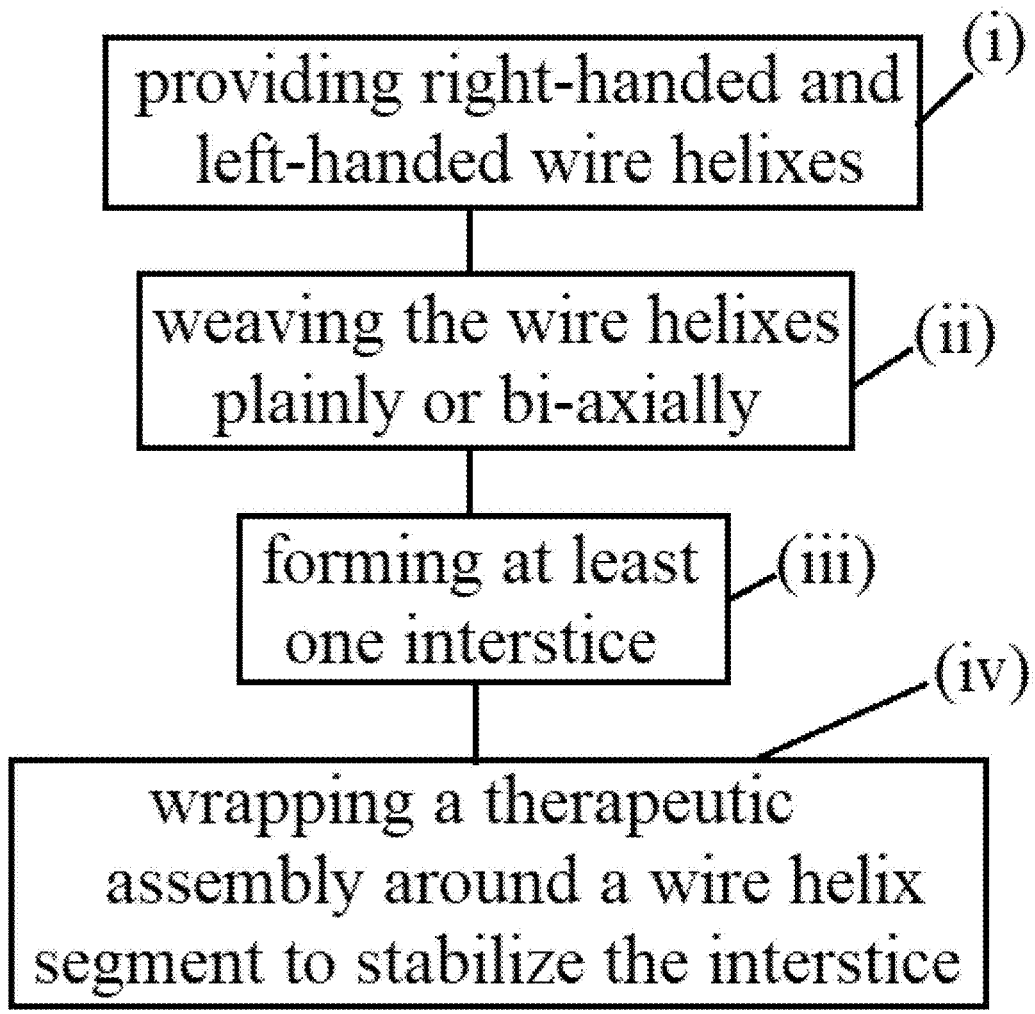
FIG. 11 is a flow chart of a general method of manufacturing a catheter apparatus used in an exemplary embodiment.

The present invention further provides a method of manufacturing the catheter apparatus as described above. As shown in FIG. 11, the method may include: (i) providing m right-handed wire helixes and n left-handed wire helixes, m≥2, and n≥2; (ii) weaving the wire helixes plainly or bi-axially into a tubular structure as the carrier; (iii) forming at least one interstice that is defined by four wire helix segments from two immediately adjacent right-handed wire helixes and two immediately adjacent left-handed wire helixes that are plainly or bi-axially woven into each other, and (iv) wrapping at least one therapeutic assembly around at least one of said four wire helix segments to stabilize the interstice.

Figure 12:
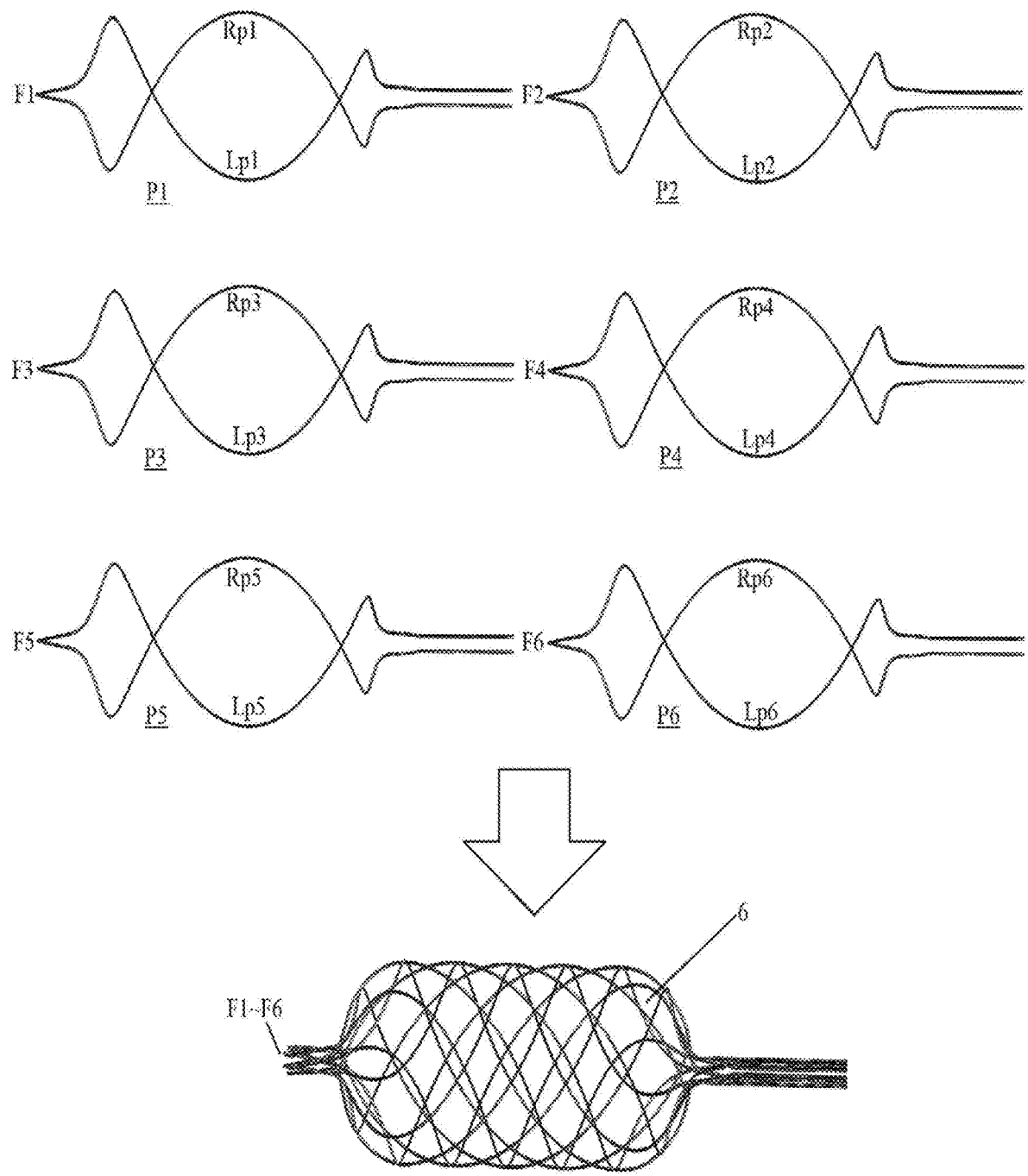
FIG. 12 demonstrates a method of manufacturing a catheter apparatus used in an exemplary embodiment.

In particularly preferred embodiments as shown in FIG. 12, at least one of the m right-handed wire helixes (e.g. one of the 6 R-helixes R1~R6, as shown in FIG. 6) and at least one of the n left-handed wire helixes (e.g. one of the 6 L-helixes L1~L6, as shown in FIG. 6) are made from one single wire, e.g. one of RL-Paired wires P1~P6. The single wire (e.g. P1) includes a first portion of right-handed wire helix Rp, e.g. one of Rp1~Rp6 that are equivalent to R1~R6; and a second portion of left-handed wire helix Lp, e.g. one of Lp1~Lp6 that are equivalent to L1~L6, by folding or bending a point (F1~F6) of the single wire (P1~P6) between the first portion and the second portion with an angle of approximately 160-180 degree.

As such, step (i) may include the steps of (ia) providing one single wire having a first portion of right-handed wire helix and a second portion of left-handed wire helix; and (ib) folding or bending the single wire at a point between the first portion and the second portion to provide a right-handed wire helix and a left-handed wire helix.

Figure 13:
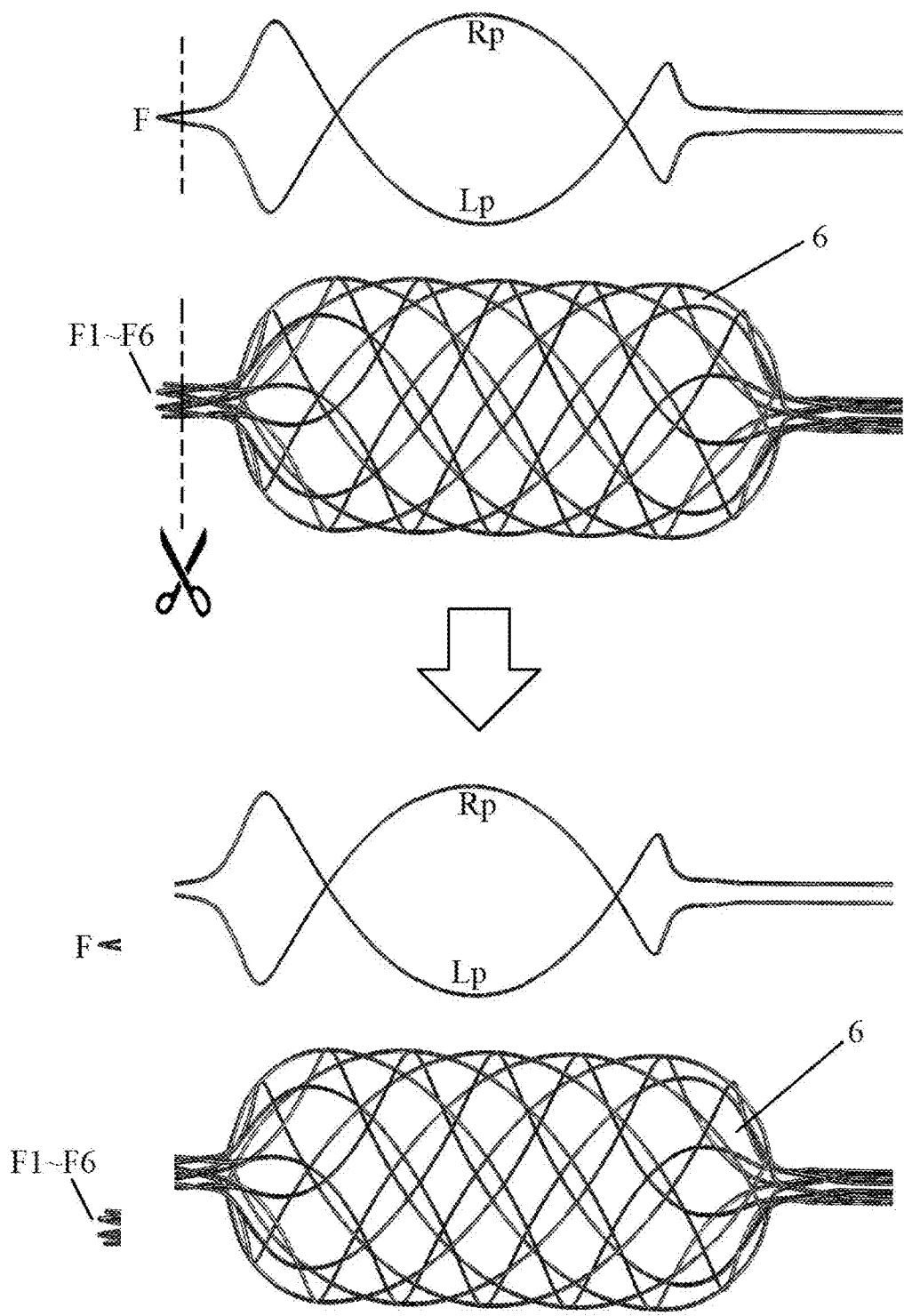
FIG. 13 demonstrates another method of manufacturing a catheter apparatus used in an exemplary embodiment.

In other particularly preferred embodiments as shown in FIG. 13, the method further includes a step of cutting the bent single wire at or near the bending point (F1~F6) to make a separate right-handed wire helix and a separate left-handed wire helix.

Figure 14:
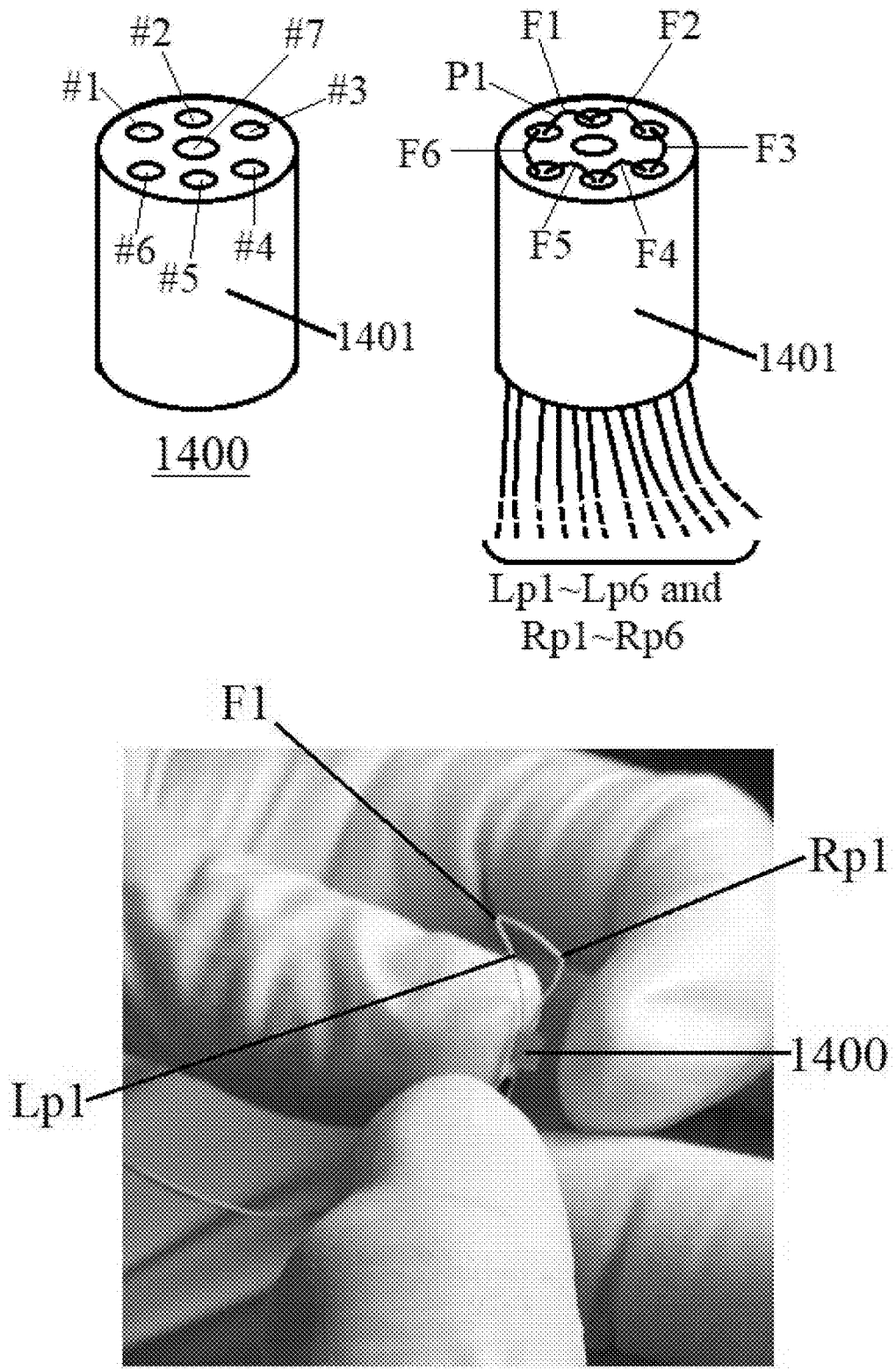
FIG. 14 illustrates the using of a multi-lumen bundler in organizing wires for weaving a carrier used in an exemplary embodiment.

In another embodiment, RL-Paired wires P1, P2, P3, P4, P5 and P6 are bundled together at their ends of the bending points using a multi-lumen bundler. Referring to FIG. 14, the multi-lumen bundler 1400 has a cylinder body 1401. A number of lumens #1~#6 pass axially through the cylinder body 1401 along the longitudinal axis of the cylinder body

1401, and may be arranged in a circular configuration. For a single RL-Paired wire, the first portion of right-handed wire helix Rp may be inserted into a lumen and pass through the lumen, and the second portion of left-handed wire helix Lp may be inserted into another lumen and pass through the lumen. The first portion of right-handed wire helix and the second portion of left-handed wire helix from a same wire may be inserted into and pass through two different lumens. The folding point or bending point of the RL-Paired wire is placed between the two mouths of the two lumens. In exemplary embodiment as shown in FIG. 14, for a single RL-Paired wire P1, the first portion of right-handed wire helix Rp1 may be inserted into lumen #1 and may pass through the lumen #1, and the second portion of left-handed wire helix Lp1 may be inserted into lumen #2 and pass through the lumen #2. The folding point or bending point F1 of the RL-Paired wire P1 is placed between the two mouths of two lumens #1 and #2, preferably F1 is located at the middle point between the two mouths of the two lumens #1 and #2. For RL-Paired wire P2, the first portion of right-handed wire helix Rp2 may be inserted into lumen #2 and may pass through the lumen #2, and the second portion of left-handed wire helix Lp2 may be inserted into lumen #3 and pass through the lumen #3. The folding point or bending point F2 of the RL-Paired wire P2 is placed between the two mouths of two lumens #2 and #3, preferably F2 is located at the middle point between the two mouths of the two lumens #2 and #3. For P3, Rp3 may be inserted into and pass through lumen #3, and Lp3 may be inserted into and pass through lumen #3. Folding point F3 is placed between the two mouths of two lumens #3 and #4, preferably at the middle point there between. For P4, Rp4 and Lp4 may be inserted into and pass through lumens #4 and #5, respectively, and F4 is placed between the two mouths of two lumens #4 and #5, preferably at the middle point there between. In a similar fashion, Rp5 and Lp5 may be inserted into and pass through lumens #5 and #6, respectively, and F5 is placed between the two mouths of two lumens #5 and #6, preferably at the middle point there between. Rp6 and Lp6 may be inserted into and pass through lumens #6 and #1, respectively, and F6 is placed between the two mouths of two lumens #6 and #1, preferably at the middle point there between. The number of wire-accepting lumens may be no less than the number of wires. The number of wire-accepting lumens may be equal to the number of wires. For example, an optional central lumen #7 in parallel with lumens #1~#6 may be included in bundler 1400, not for accepting any RL-Paired wire, but for e.g. control wire or pull/push wire 19 to pass through, if needed. After RL-Paired wires P1~P6 are properly placed in lumens #1~#6 as described above, a liquid adhesive material may be filled into or dropped into lumens #1~#6. After the liquid adhesive material is solidified, RL-Paired wires P1~P6 will be permanently glued and fixed to multi-lumen bundler 1400.

Figure 15:
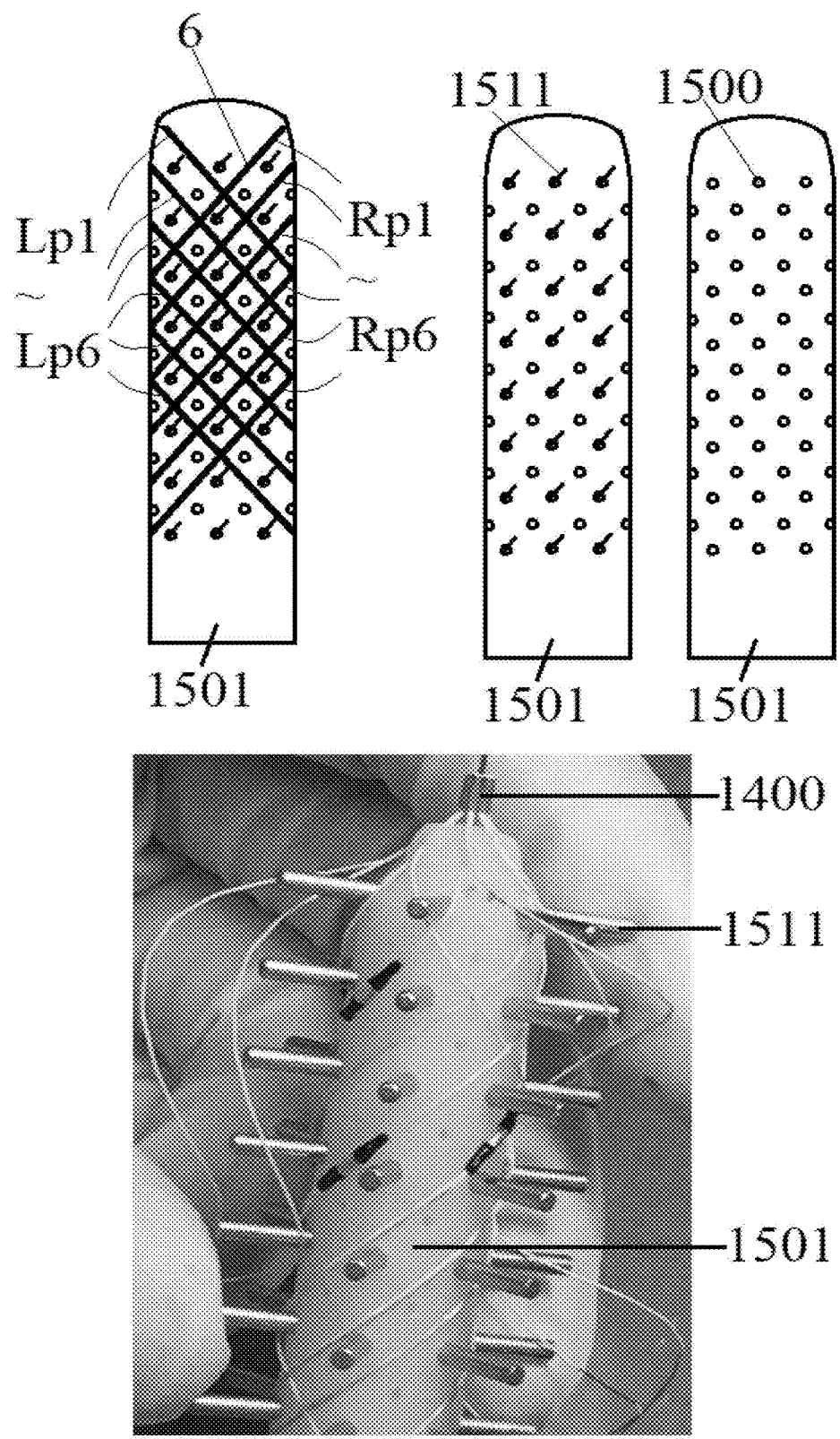
FIG. 15 illustrates the using of a bobbin and a multi-lumen bundler in weaving wire helixes plainly or bi-axially into a tubular structure in accordance with an exemplary embodiment.

When step (ii), i.e. weaving the wire helixes plainly or bi-axially into a tubular structure as the carrier, is implemented, a bobbin may be used as a scaffold. As shown in FIG. 15, a bobbin 1501 has an array of holes 1500 on it, for pins 1511 to insert in. Between any two pins 1500, or two rows of pins 1500, a wire such as one of P1~P6 may be wound. The pins 1500 may function as flanges for bobbin 1501. Multi-lumen bundler 1400 may optionally be used with bobbin 1501. When it is used, multi-lumen bundler 1400 with loose RL-Paired wires P1~P6 is placed on top tip of the bobbin 1501, and functions as the start point of the weaving process. After the weaving process is completed, pins 1511 are removed from bobbin 1501, leaving behind a tubular structure as the carrier of the invention.

EXAMPLES

In the present study, 5 ED patients received Endovascular Arterial Denervation (EDN) treatment with the use of a radiofrequency denervation system with a novel multi-electrode mesh catheter, as described above. All of the patients experienced improved penile erection after EDN. The internal iliac artery is a short, thick vessel, smaller than the external iliac artery, and is about 3 to 4 cm in length. The internal iliac artery (hypogastric artery) is the main artery of the pelvis, and it supplies the walls and viscera of the pelvis, the buttock, the reproductive organs, and the medial compartment of the thigh. The vesicular branches of the internal iliac arteries supply the bladder.

Figure 16:
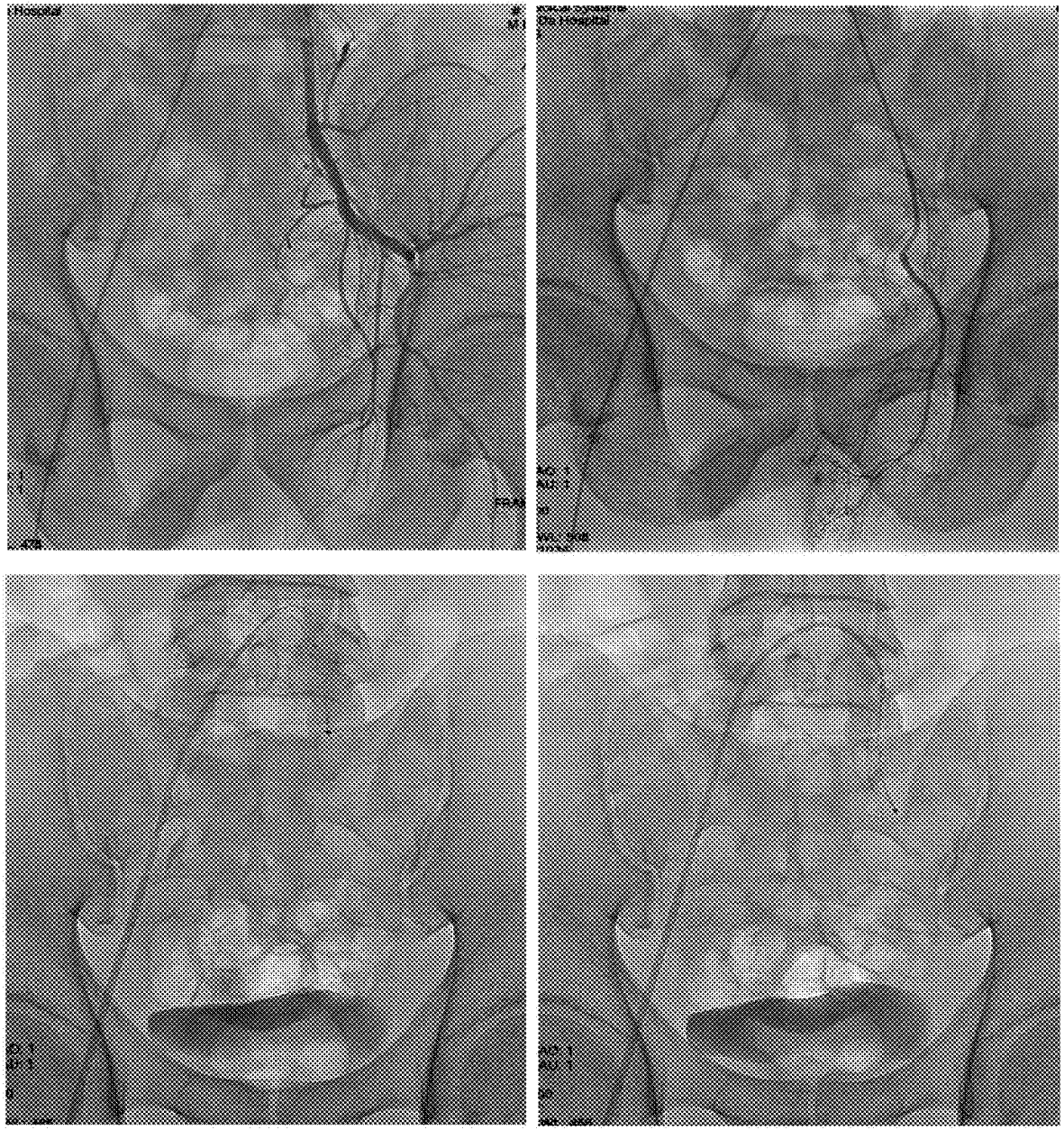
FIG. 16 shows representative digital subtraction angiography of the internal iliac artery during a procedure in accordance with an exemplary embodiment of the present invention.

FIG. 16 are the images during a treatment procedure, from which it can be seen that 6 electrodes were placed within a beginning segment of internal iliac artery or hypogastric artery. After 6 ablation electrodes #1~#6 (from top to down) were placed within the target segment of the internal iliac artery of the patient and against blood vessel wall thereof and a surface electrode was adhered on the skin of the patient's back, the treatment procedure was initiated. For each of the electrodes #1~#6, the ablation target temperature was set as 60° C., the ablation period was set as 60 or 120 seconds, the ablation power was adjusted (increased as needed, or decreased if too high) during the ablation period with a ceiling of 9 W, the ablation frequency was set as 465 KHz. The impedance between the surface electrode and electrodes #1~#6 varied from electrode to electrode and from one real time to another real time, but typically within the range of 200-320 Ohms.

Every time, only one of 6 internal electrodes was activated. The 6 internal electrodes took turn to work. A thermal couple was placed inside each of the internal electrodes to measure the "electrode temperature". If the electrode temperature could not rise to the preset temperature anyway and the power reached the maximum level 9 W, a judgement was made that the electrode did not intimately contact the blood vessel internal wall. The procedure then started over, and the catheter was adjusted so that the electrode can contact intimately to the blood vessel internal wall. Sometimes, the position of the catheter was adjusted, and the ablation was repeated once more to guarantee a good therapeutic result. The ablation may be repeated for a few times or sessions. For example, in the first session, some (or even all) internal electrodes did not intimately contact the blood vessel internal wall and, for other internal electrodes, the electrode temperature could not rise to the target temperature and the power reached the maximum level 9 W. Therefore, the catheter position was adjusted, and the basket supporting the internal electrodes (i.e. carrier 6) was expanded bigger.

A surface electrode was placed on the back of the patient and connected to the denervation device. CT imaging may be performed to identify the internal iliac artery by means of transfemoral access with the use of an 8-F sheath and 5-F pigtail catheter. Then the EDN 6-electrode catheter (Golden Leaf, Shanghai) was inserted to the target segment. This multi-electrode EDN catheter has 6 electrodes helically on a net structure, and the ablation electrodes can expand according to internal iliac artery diameters and stick to the artery wall by drawing and rotating the catheter basket. The catheter was connected to the denervation device. The patients were under moderate sedation with combinations of intravenous midazolam and/or oxycodone when EDN started. Denervation was carried out with ablation parameters set at time 60 or 120 seconds and temperature 60° C. The internal iliac artery was treated with 6 points of ablation, separately. After completion of the ablation, the puncture site was closed with the use of Proglide vascular closure devices (Abbott Vascular, Abbott Park, Illinois).

Figure 17:
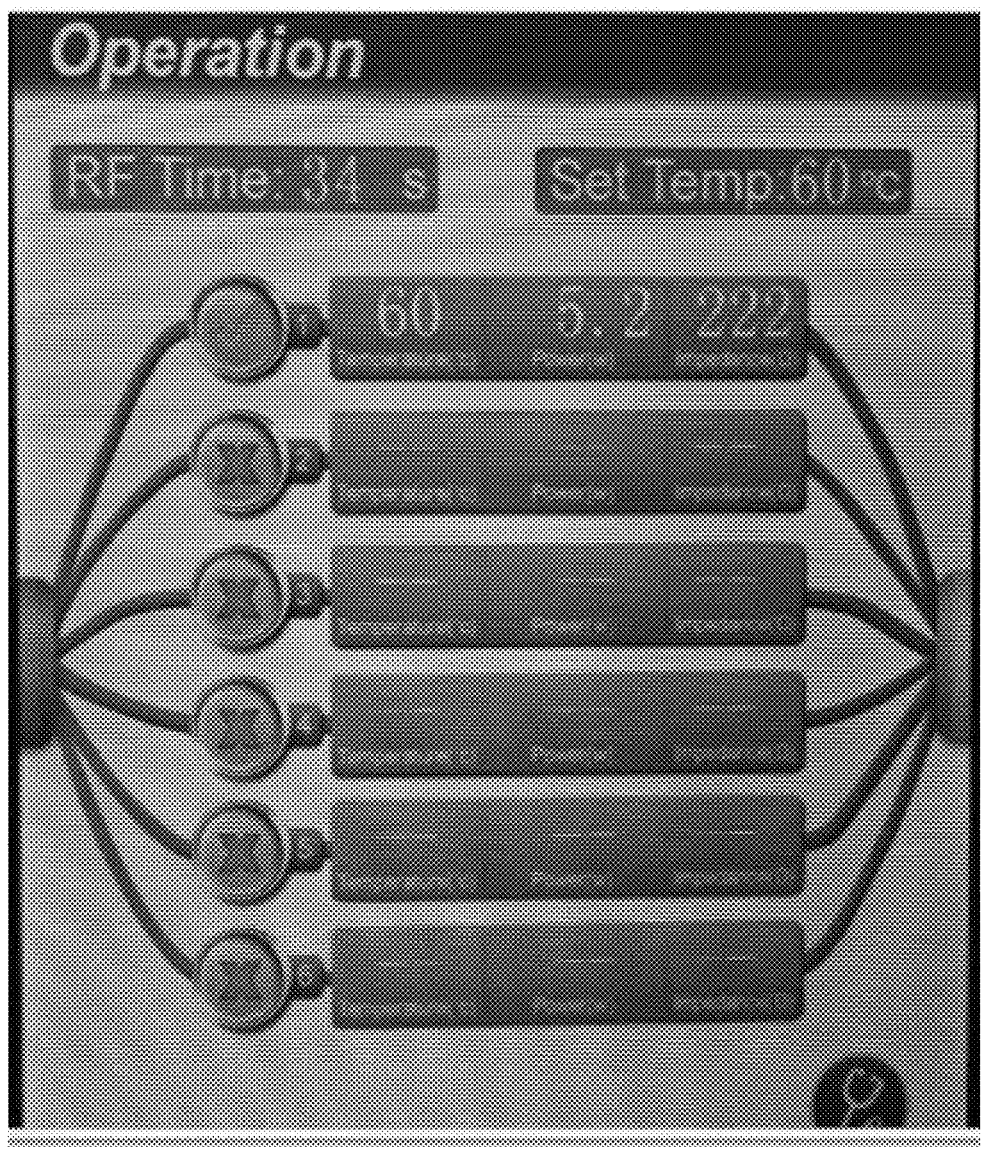
FIG. 17 displays the controlling of parameters of a treatment procedure in accordance with an exemplary embodiment of the present invention.

As shown in FIG. 17, electrode #1 was turned on while electrodes #2-6 were turned off, with a set of parameters (temperature 60° C., RF period 60 seconds). At a given real-time time such as when RF time was 34 seconds (t=34 seconds), the real-time impedance between the surface electrode and electrode #1 was 222 Ohms, the real-time temperature was 60° C. (as desired), and the real-time power was 5.2 W (as desired, because it was below ceiling of 9 W).

Figure 18:
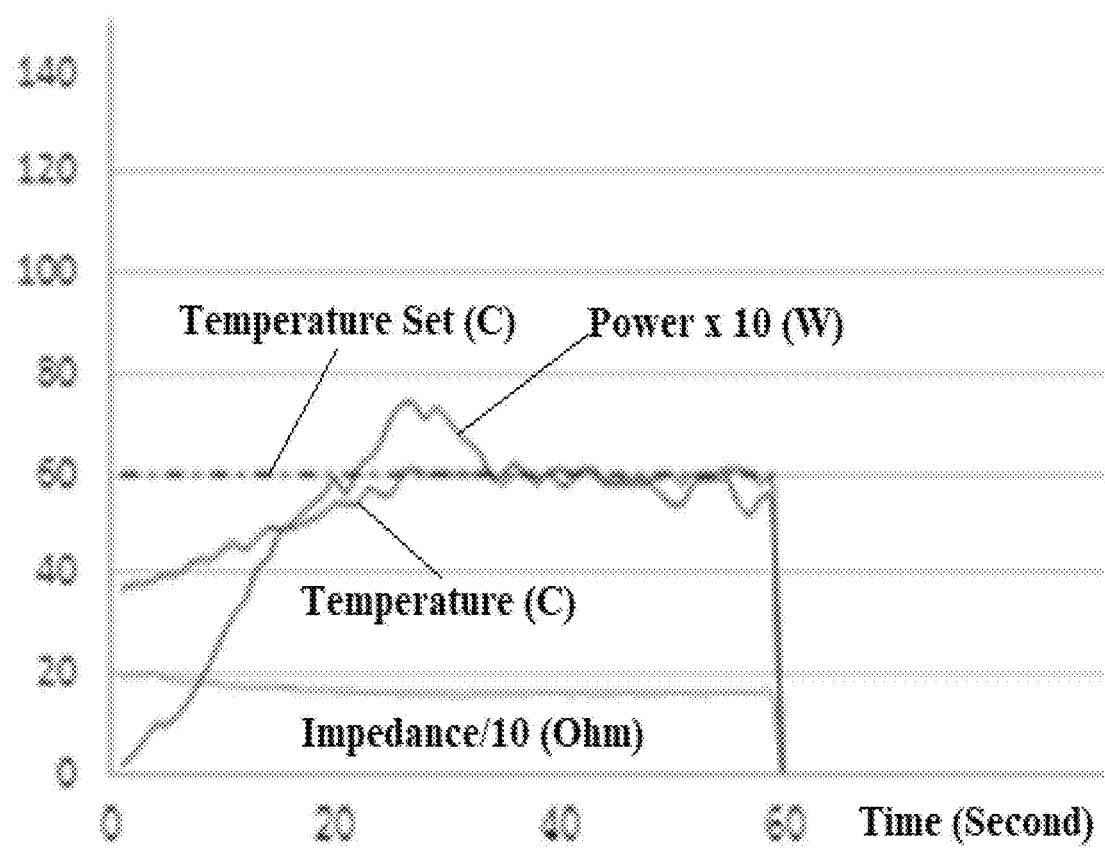
FIG. 18 is a plot showing a representative protocol of a treatment procedure including power, temperature, and impedance as a function of time in accordance with an exemplary embodiment of the present invention.
Figure 19A:
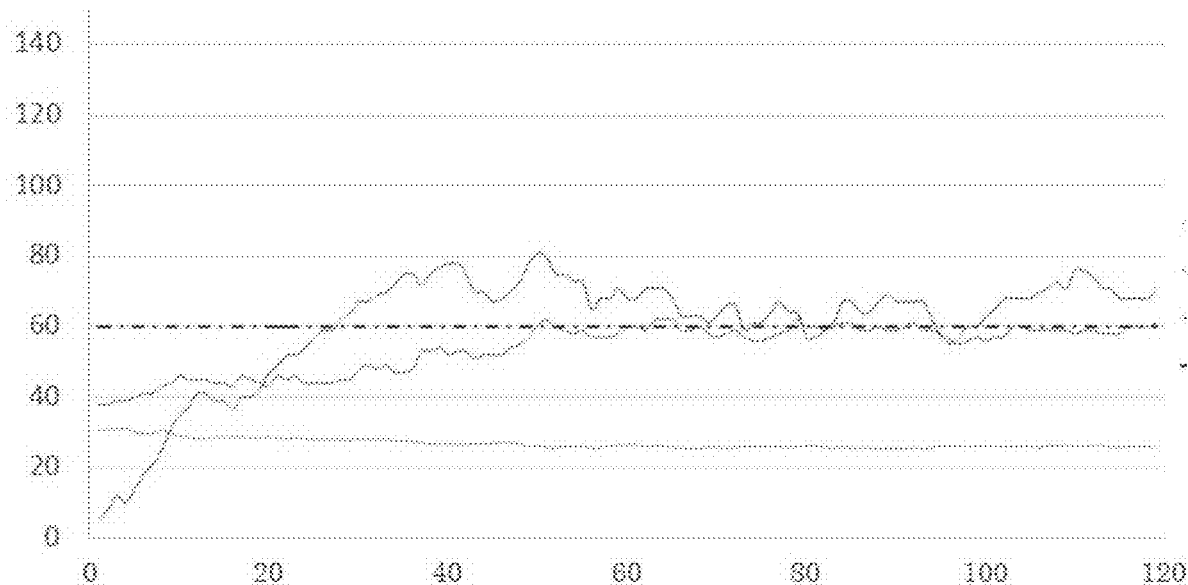
FIG. 19A shows a first part of representative protocols including power, temperature, and impedance as a function of time during a procedure in accordance with an exemplary embodiment of the present invention.
Figure 19A:
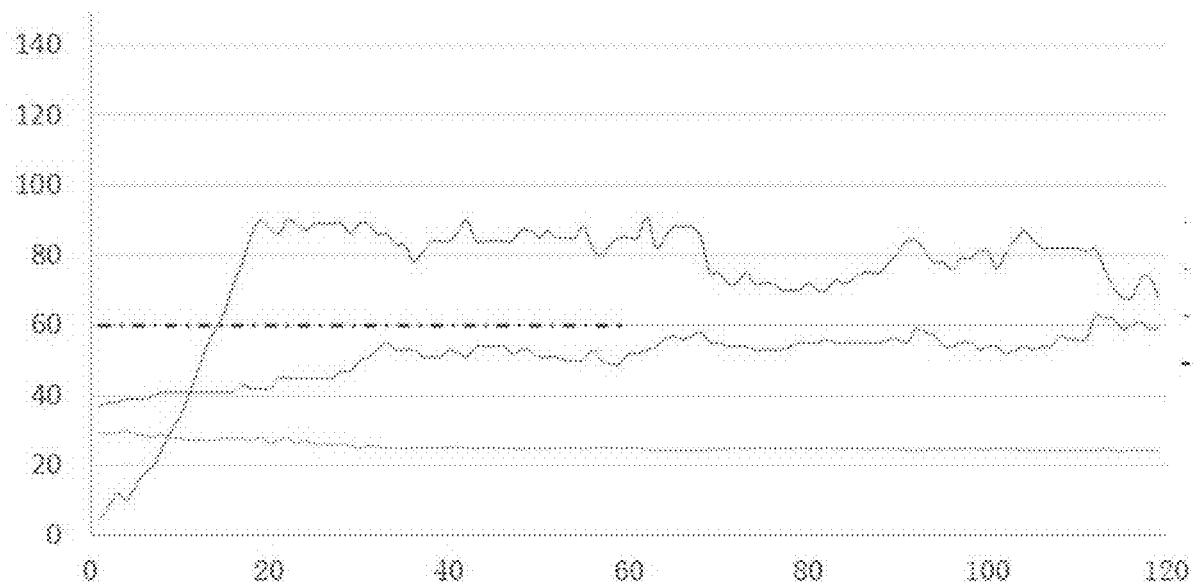
Figure 19B:
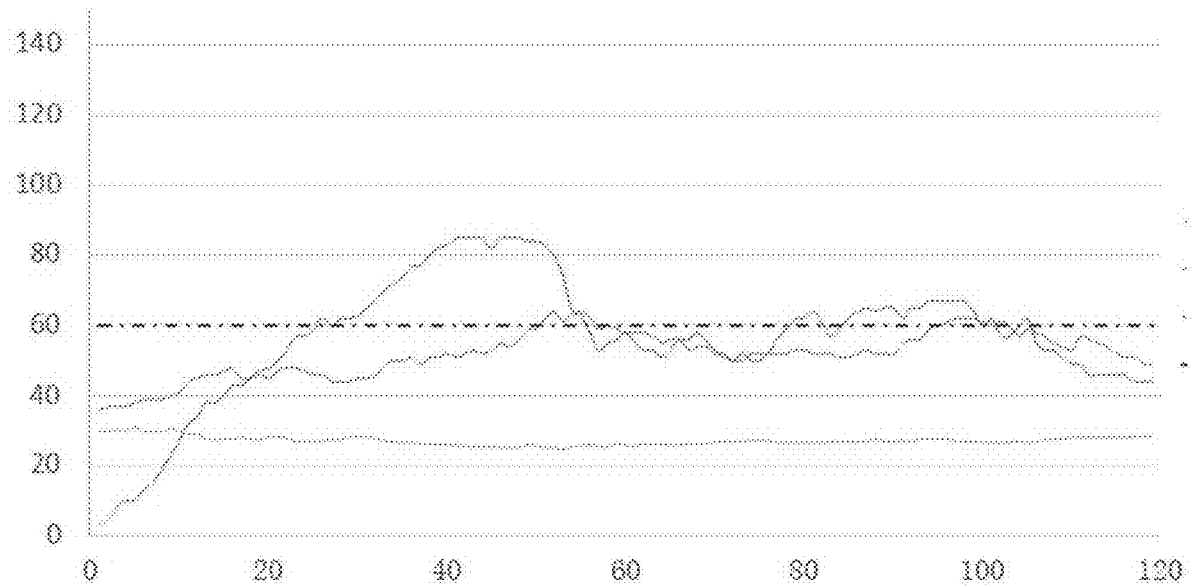
FIG. 19B shows a second part of representative protocols including power, temperature, and impedance as a function of time during a procedure in accordance with an exemplary embodiment of the present invention.
Figure 19B:
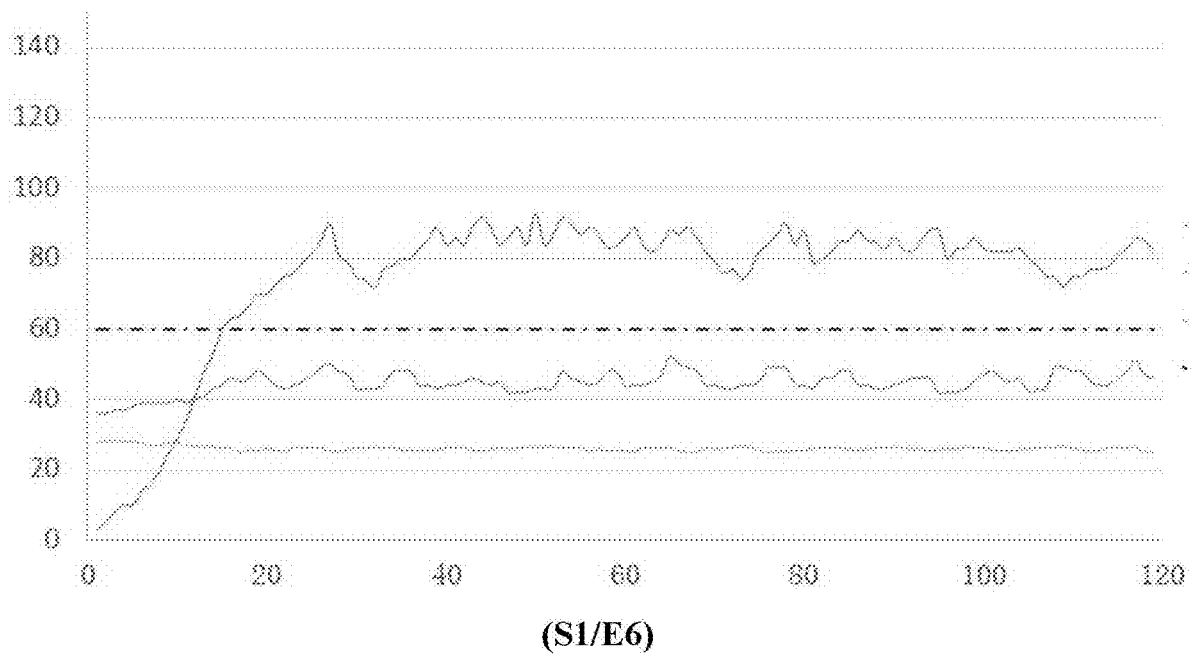
Figure 19C:
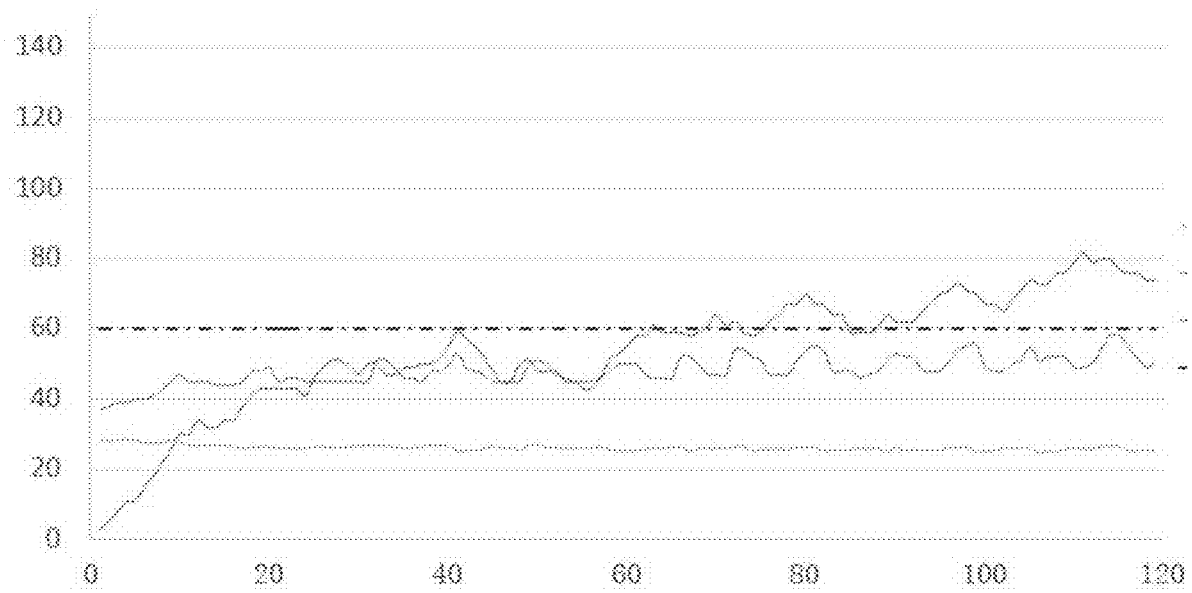
FIG. 19C shows a third part of representative protocols including power, temperature, and impedance as a function of time during a procedure in accordance with an exemplary embodiment of the present invention.
Figure 19C:
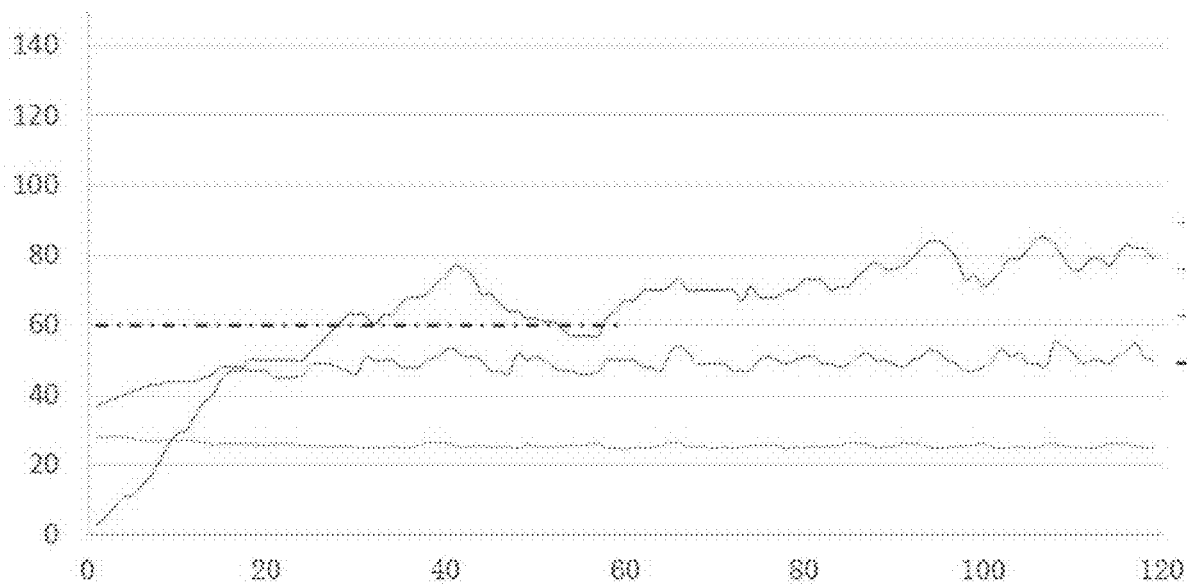
Figure 19D:
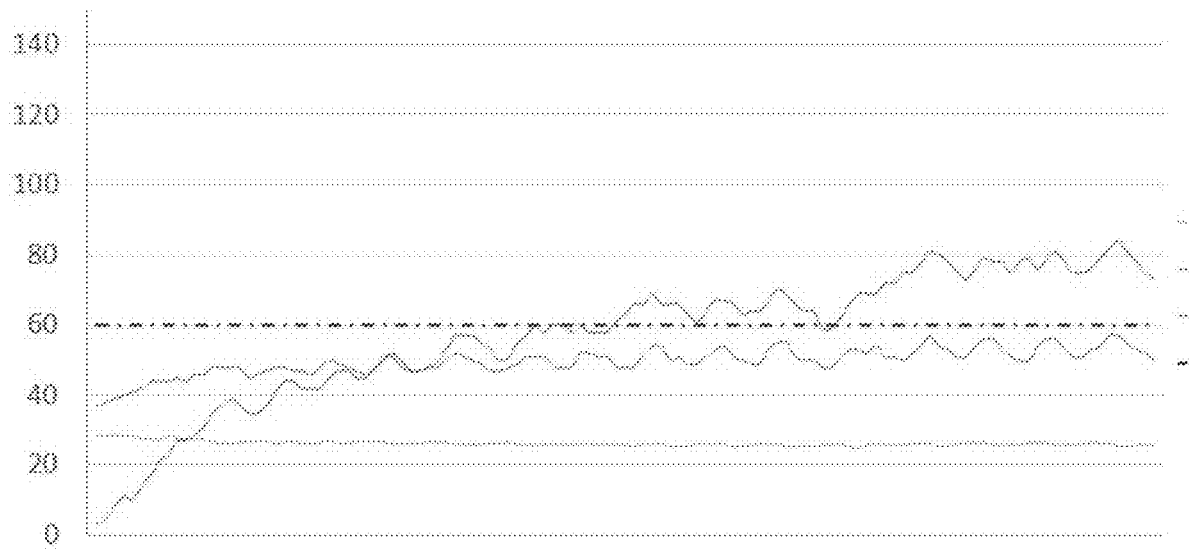
FIG. 19D shows a fourth part of representative protocols including power, temperature, and impedance as a function of time during a procedure in accordance with an exemplary embodiment of the present invention.
Figure 19D:
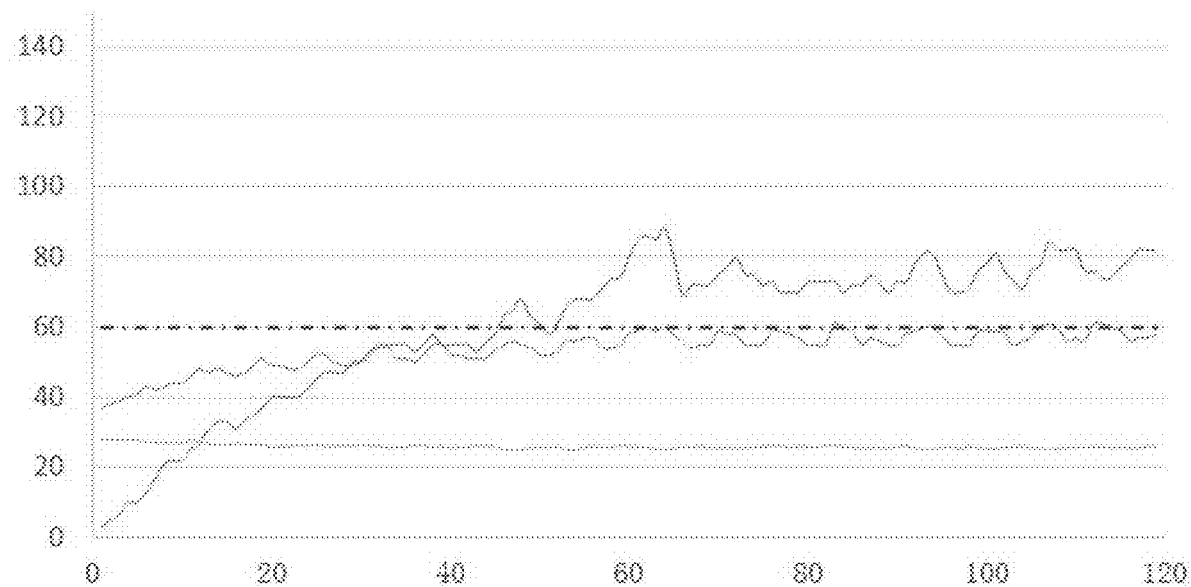
Figure 19E:
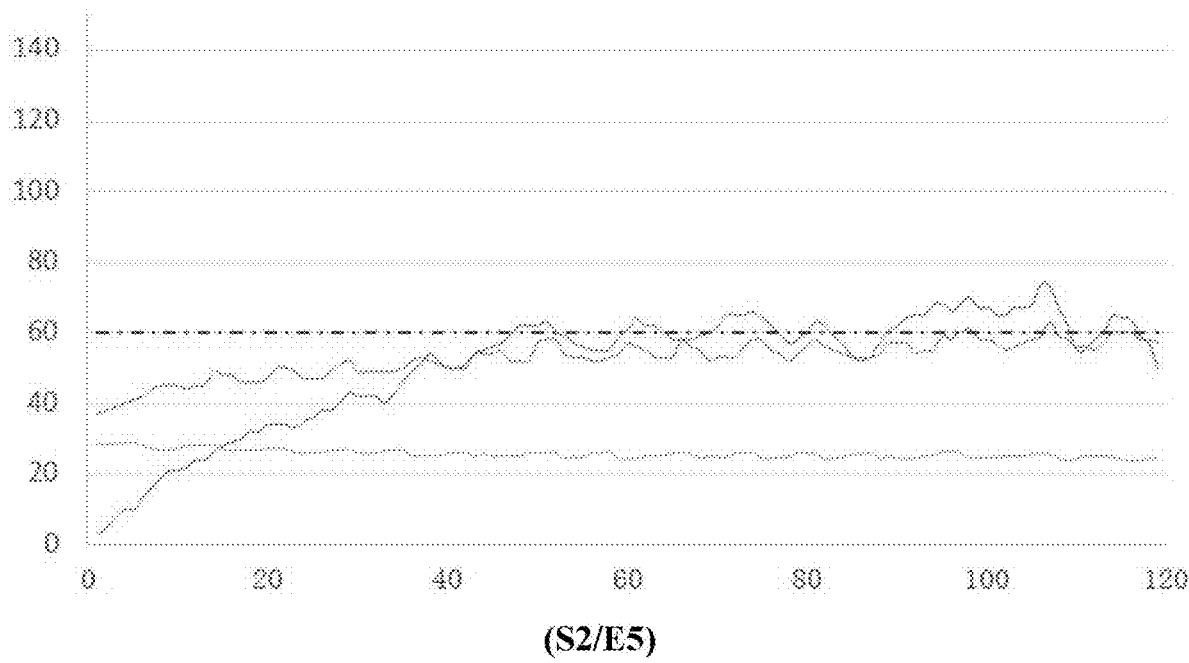
FIG. 19E shows a fifth part of representative protocols including power, temperature, and impedance as a function of time during a procedure in accordance with an exemplary embodiment of the present invention.
Figure 19E:
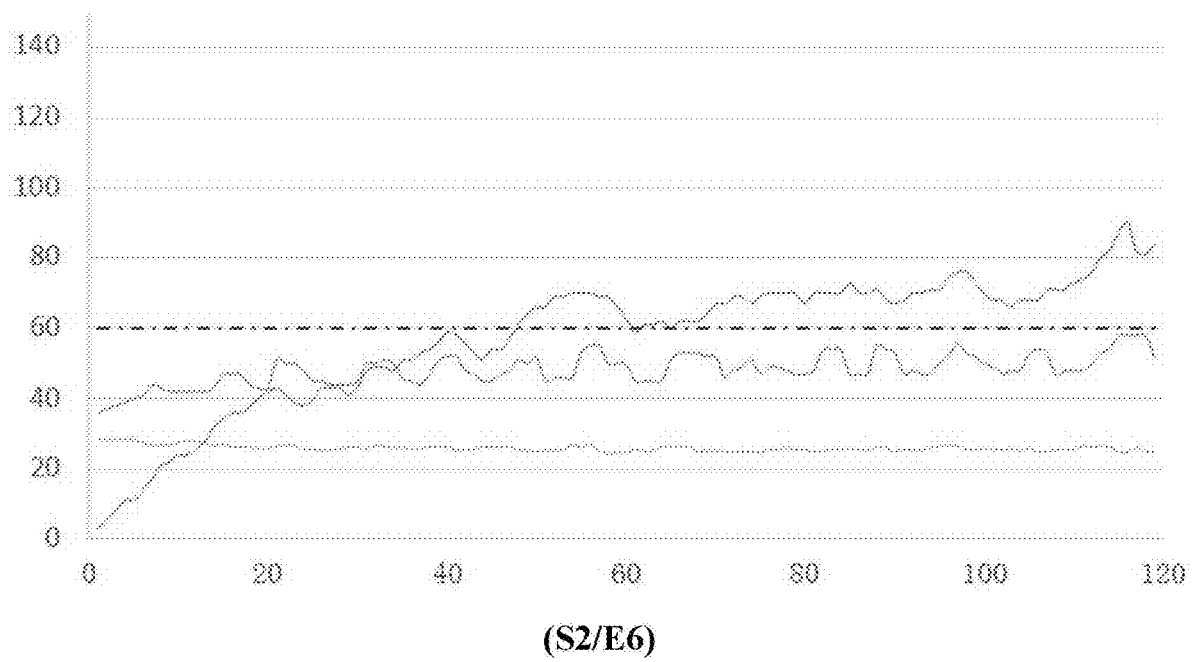

As shown in FIG. 18, the power with electrode #1 has been increased from 0 at t=0 to 7.7 W at t=28 sec, and the temperature has been increased from body temperature (BT) 37 C at t=0 to 60 C at t=28 sec. The power has been decreased from 7.7 W at t=28 sec down to 5.2 W at t=60 sec, and the temperature has been maintained around 60 C from t=28 sec to t=60 sec. The impedance between the surface electrode and electrode #1 has been decreased from 200 Ohms at t=0 to 160 Ohms at t=60 sec. Such a protocol will be simply described as: Power increases from 0 to 7.7 W (t=0-28) and decreases from 7.7 W to 5.2 W (t=28-60); Temperature increases from BT to 60 C (t=0-28) and stays around 60 C for 32 seconds (t=28-60); and Impedance decreases from 200 to 160 Ohms (t=0-60). Other treatment protocols will be described in a similar fashion.

Example 1: ED Patient #1

For patient #1, the entire treatment protocol includes two sessions, as shown in FIGS. 19A-19E and summarized in the Table below. The time period for non-ablative thermal alteration (<45° C.) is defined as Tna, the time period for ablative thermal alteration (≥45° C.) is defined as Ta, and the ratio between the two is defined as Rna/a.

| Treatment Protocol for Patient #1 | |
| --- | --- |
| Session #/ Electrode # (S#/E#) | Protocol for Patient #1 |
| S1/E1 | Rna/a = 10:110 (seconds): Temperature increases from BT to 60 C. (t = 0-50) and stays 60 C. for 70 seconds (t = 50-120); Power increases from 0 to 8 W (t = 0-50) and decreases from 8 W to 7 W (t = 50-120); Impedance decreases from 310 to 270 Ohms (t = 0-120). |
| S1/E2 | Rna/a = 25:95 (seconds): Temperature increases from BT to 60 C. (t = 0-117) and stays 60 C. for 3 seconds (t = 117-120); Power increases from 0 to 9 W (t = 0-20) and decreases from 9 W to 7 W (t = 20-120); Impedance decreases from 300 to 250 Ohms (t = 0-120). |
| S1/E5 | Rna/a = 10:110 (seconds): Temperature increases from BT to 60 C. (t = 0-55) and decreases to 50 C. (t = 55-120); Power increases from 0 to 8.6 W (t = 0-42) and decreases from 8.6 W to 4.5 W (t = 42-120); Impedance decreases from 310 to 295 Ohms (t = 0-120). |
| S1/E6 | Rna/a = 15:105 (seconds): Temperature increases from BT to 50 C. (t = 0-30) and stays 50 C. for 90 seconds (t = 30-120); Power increases from 0 to 8.7 W (t = 0-25) and decreases from 8.7 W to 8.3 W (t = 25-120); Impedance decreases from 290 to 270 Ohms (t = 0-120). |
| S2/E1 | Rna/a = 10:110 (seconds): Temperature increases from BT to 50 C. (t = 0-35) and stays 50 C. for 85 seconds (t = 35-120); Power increases from 0 to 8 W (t = 0-115) and decreases from 8 W to 7.5 W (t = 115-120); Impedance decreases from 295 to 250 Ohms (t = 0-120). |
| S2/E2 | Rna/a = 10:110 (seconds): Temperature increases from BT to 50 C. (t = 0-30) and stays 50 C. for 90 seconds (t = 30-120); Power increases from 0 to 7.8 W (t = 0-40) and stays around 8 W (t = 40-120); Impedance decreases from 290 to 250 Ohms (t = 0-120). |
| S2/E3 | Rna/a = 10:110 (seconds): Temperature increases from BT to 50 C. (t = 0-35) and stays around 50 C. for 85 seconds (t = 35-120); Power increases from 0 to 7.7 W (t = 0-95) and stays around 7.7 W (t = 95-120); Impedance decreases from 295 to 255 Ohms (t = 0-120). |
| S2/E4 | Rna/a = 10:110 (seconds): Temperature increases from BT to 58 C. (t = 0-60) and stays around 58 C. for 60 seconds (t = 60-120); Power increases from 0 to 7.5 W (t = 0-60) and stays around 7.5 W thereafter (t = 60-120); Impedance decreases from 290 to 255 Ohms (t = 0-120). |
| S2/E5 | Rna/a = 5:115 (seconds): Temperature increases from BT to 58 C. (t = 0-50) and stays around 56-60 C. for 70 seconds (t = 50-120); Power increases from 0 to 6 W (t = 0-50) and stays around 6 W thereafter (t = 50-120); Impedance decreases from 290 to 250 Ohms (t = 0-120). |
| S2/E6 | Rna/a = 15:105 (seconds): Temperature increases from BT to 50 C. (t = 0-40) and stays around 50-58 C. for 80 seconds (t = 40-120); Power increases from 0 to 7 W (t = 0-55) and stays around 6-9 W thereafter (t = 55-120); Impedance decreases from 290 to 250 Ohms (t = 0-120), |

Nocturnal penile tumescence (NPT) test was used to evaluate the efficacy of the treatment for Patient #1. When a man has problems with erections, it is sometimes difficult to know if the cause(s) are physical, psychological, or both. The nocturnal penile tumescence (NPT) test can give the doctor some clues. Nocturnal penile tumescence is a spontaneous erection of the penis during sleep or when waking up. All men without physiological erectile dysfunction experience nocturnal penile tumescence, usually three to five times during a period of 8-hour sleep, typically during rapid eye movement sleep. The NPT test shows whether these erections have occurred. The test may be done at home or at a sleep lab. An accurate method involves a special electronic device with two rings connected to it. One ring is placed at the tip of the penis; the other is placed at the base. While the man sleeps, the device monitors his nocturnal erections, including how many occur, how long they last, and how rigid they are. The traces are then analyzed by the machine and the results interpreted by trained clinicians and practitioners in order to determine erectile function. The fact that a man has normal nocturnal erections shows that his body is working normally, and it is likely that psychological issues are affecting his erectile function.

NPT test for Patient #1 uses standard Rigiscan Campbell Urology 2006, and the results are summarized in the table below.

| NPT Test Results (Patient #1) | Before Treatment | After Treatment |
| --- | --- | --- |
| Monitoring Time Length | 10 hours | 10 hours |
| Erection Time Length | 6 minutes | 43 minutes |
| Erection Frequency | 1 Time | 3 Times |
| Mean Erection Rigidity % - Penis Tip | 38 | 66 |
| Time Length with Rigidity ≥ 80% (Penis Tip) | 0.5 minute | 5.5 minutes |
| Time Length with Rigidity ≥ 60% (Penis Tip) | 1 minute | 27.5 minutes |
| Mean Erection Rigidity % - Penis Base | 47 | 56 |
| Time Length with Rigidity ≥ 80% (Penis Base) | 1 minute | 0.5 minute |
| Time Length with Rigidity ≥ 60% (Penis Base) | 1 minute | 24.5 minutes |

Figure 20A:
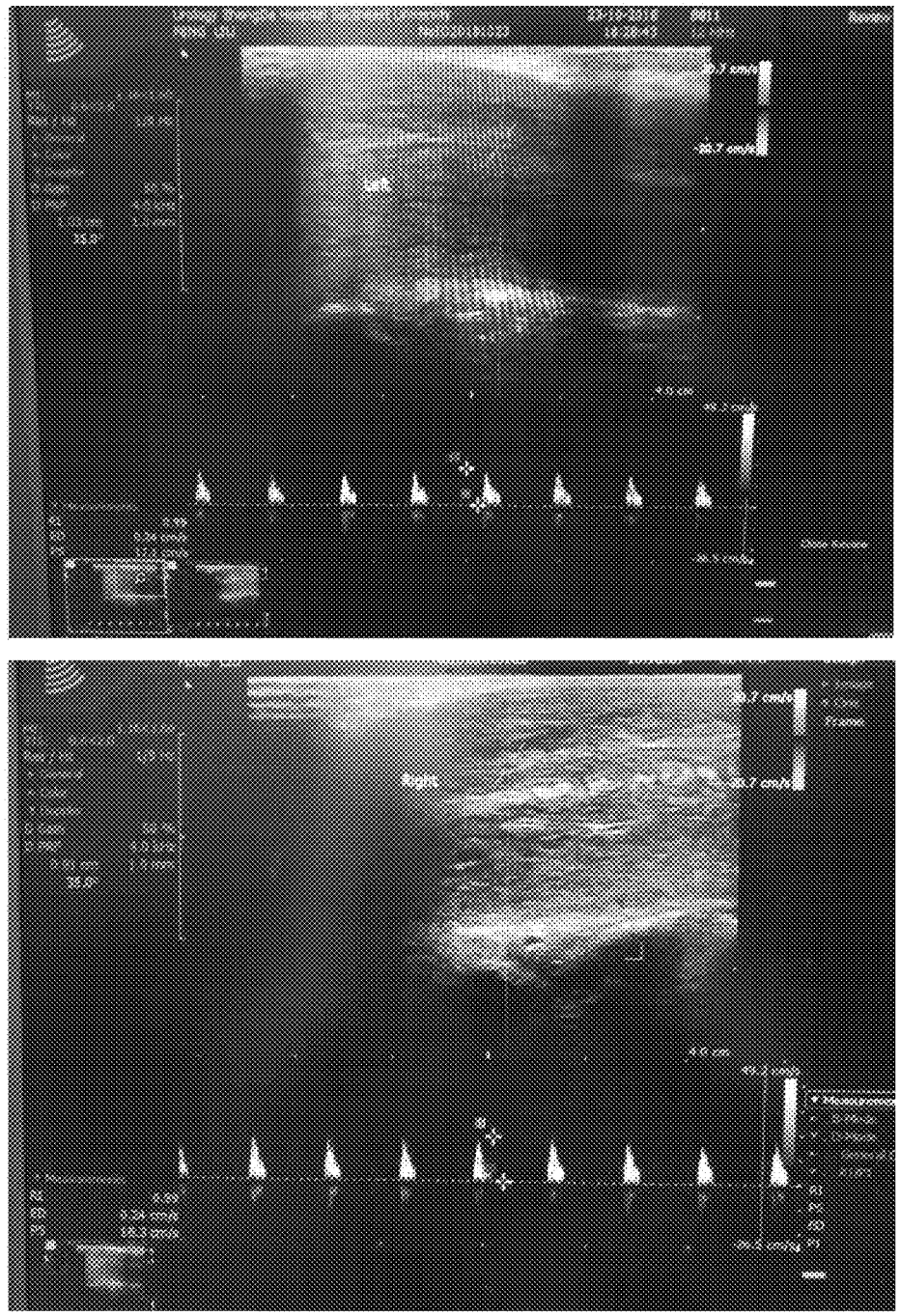
FIG. 20A shows ultra sound images of an ED patient before a treatment in accordance with an exemplary embodiment of the present invention.
Figure 20B:
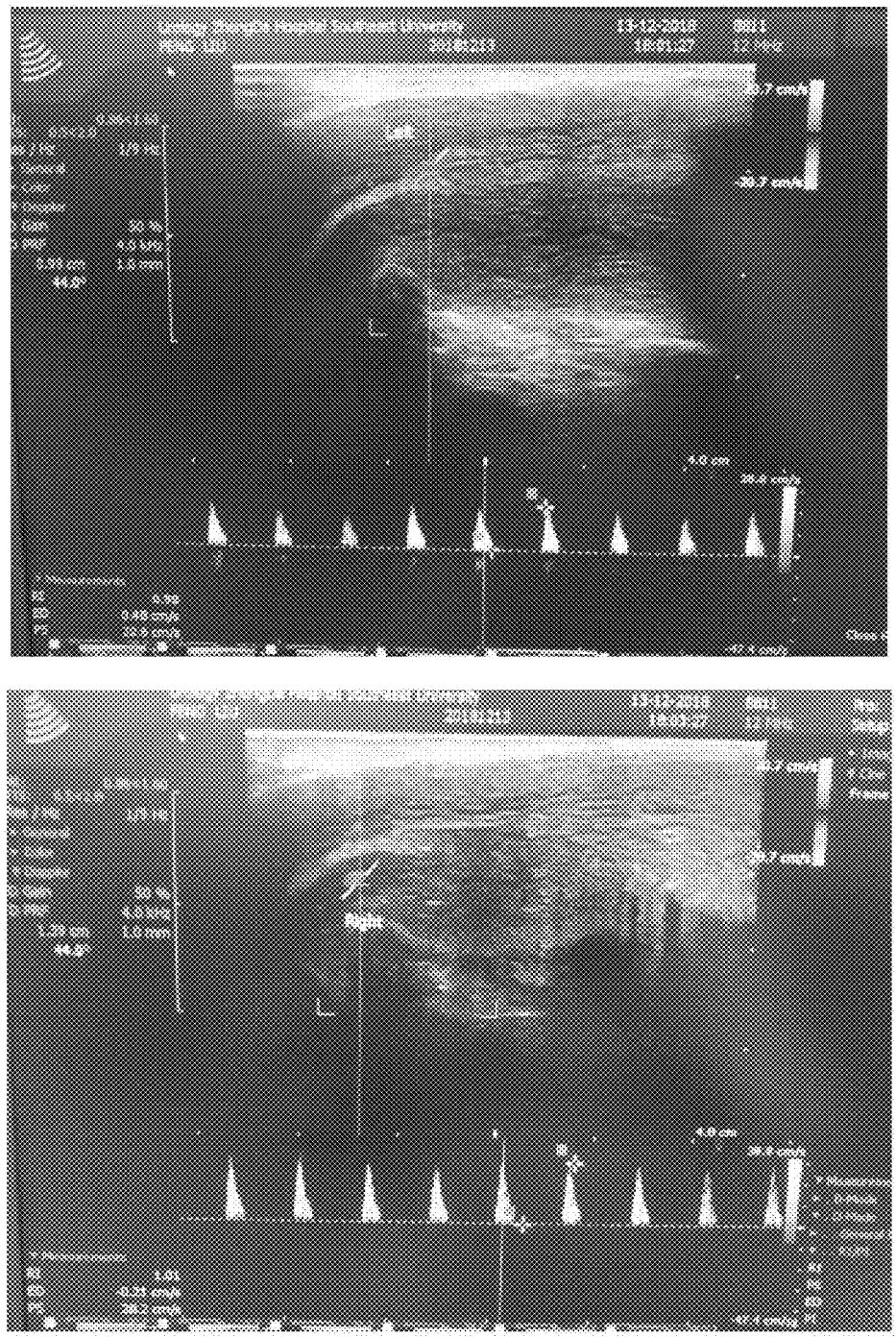
FIG. 20B shows ultra sound images of an ED patient after a treatment in accordance with an exemplary embodiment of the present invention.

As shown in the table above, the Erection Time Length, Erection Frequency, and Erection Rigidity have all been significantly improved. Ultrasound Doppler color images for patient #1 as shown in FIGS. 20A and 20B show the improvement of blood flow as well. An ultrasound is an imaging test that uses sound waves to produce pictures of internal organs, giving doctors a more detailed view. Penile ultrasound can be used to evaluate many conditions affecting the penis, including erectile dysfunction (ED), plaques (such as those caused by Peyronie's disease), fibrosis, lumps, and even cancer. Men with erection problems often have a Doppler ultrasound, which can show the way blood flows in and out of organs. In a Doppler ultrasound, the sound waves bounce off circulating red blood cells. A change in pitch signals the movement of blood. The test begins with an injection of medicine, which causes an erection by widening arteries and increasing blood flow. From there, a doctor moves a small device called a transducer over against the skin of the penis. The transducer sends data to a computer so that the doctor can tell how fast blood is flowing in and out. If the induced erection lasts longer than the test, the doctor might give another injection so the penis will become flaccid again.

Example 2: ED Patient #2

Similar to patient #1, the entire treatment protocol for patient #2 includes three sessions, as summarized in the Table below.

| Session #/ Electrode # (S#/E#) | Protocol for Patient #2 |
| --- | --- |
| S1/E1 | Rna/a = 72:48 (seconds): Temperature increases from BT to 45 C. (t = 0-20), stays around 45 C. for 80 seconds (t = 20-72), and jumps to and stays at 60 C. thereafter (t = 72-120); Power increases from 0 to 8.5 W (t = 0-25), stays around 8.5 W for 47 seconds (t = 25-72), and drops to and stays around 2.5-3 W thereafter (t = 72-120), Impedance decreases from 290 to 270 Ohms (t = 0-120). |
| S1/E2 | Rna/a = 10:110 (seconds): Temperature increases from BT to 55 C. (t = 0-45), stays around 55 C. for 75 seconds thereafter (t = 45-120); Power increases from 0 to 6 W (t = 0-58), and drops to around 4 W thereafter (t = 58-120); Impedance decreases from 280 to 245 Ohms (t = 0-120). |
| S1/E3 | Rna/a = 25:95 (seconds): Temperature increases from BT to 60 C. (t = 0-60), and stays around 60 C. thereafter (t = 60-120); Power increases from 0 to 9 W (t = 0-30), and drops to around 5.5 W thereafter (t = 30-120); Impedance decreases from 290 to 250 Ohms (t = 0-120). |
| S1/E4 | Rna/a = 6:114 (seconds): Temperature increases from BT to 60 C. (t = 0-55), and stays around 60 C. thereafter (t = 55-120); Power increases from 0 to 5 W (t = 0-50), and stays around 5 W thereafter (t = 50-120); Impedance decreases from 300 to 270 Ohms (t = 0-120). |
| S1/E5 | Rna/a = 30:90 (seconds): Temperature increases from BT to 45 C. (t = 0-25), stays around 45 C. for 80 seconds (t = 25-77), and jumps to and stays at 60 C. thereafter (t = 77-120); Power increases from 0 to 8.5 W (t = 0-20), stays around 8.5 W for 57 seconds (t = 20-77), and drops to and stays around 2.5-3 W thereafter (t = 77-120); Impedance stays around 270-300 Ohms (t = 0-120). |
| S1/E6 | Rna/a = 18:102 (seconds): Temperature increases from BT to 45 C. (t = 0-18), and stays around 45 C. thereafter (t = 18-120); Power increases from 0 to 8.8 W (t = 0-20), and stays around 8.5-8.8 W thereafter (t = 20-120); Impedance decreases from 285 to 250 Ohms (t = 0-120). |
| S2/E1 | Rna/a = 25:95 (seconds): Temperature increases from BT to 45 C. (t = 0-25), and stays around 45 C. thereafter (t = 25-120); Power increases from 0 to 8.5 W (t = 0-25), and stays around 8.5 W thereafter (t = 25-120); Impedance decreases from 290 to 270 Ohms (t = 0-120). |

| Session #/<br>Electrode #<br>(S#/E#) | Protocol for Patient #2 |
|---|---|
| S2/E2 | Rna/a = 5:115 (seconds): Temperature increases from BT to 58 C. (t = 0-40), and stays around 58 C. thereafter (t = 40-120); Power increases from 0 to 4 W (t = 0-35), and drops from 4 W to 3 W thereafter (t = 72-120); Impedance decreases from 270 to 250 Ohms (t = 0-120). |
| S2/E3 | Rna/a = 20:100 (seconds): Temperature increases from BT to 50 C. (t = 0-77), and jumps to and stays at 58 C. thereafter (t = 77-120); Power increases from 0 to 8.5 W (t = 0-40), stays around 8.5 W for 38 seconds (t = 40-78), and drops to and stays around 4-5 W thereafter (t = 78-120); Impedance decreases from 290 to 210 Ohms (t = 0-120). |
| S2/E4 | Rna/a = 15:105 (seconds): Temperature increases from BT to 60 C. (t = 0-80), and stays around 60 C. thereafter (t = 80-120); Power increases from 0 to 8.5 W (t = 0-25), stays around 8.5 W for 47 seconds (t = 25-72), and drops to and stays around 5-6.2 W thereafter (t = 72-120); Impedance decreases from 290 to 240 Ohms (t = 0-120). |
| S2/E5 | Rna/a = 15:105 (seconds): Temperature increases from BT to 50 C. (t = 0-85), and jumps to and stays around 60 C. thereafter (t = 87-120); Power increases from 0 to 8.7 W (t = 0-60), stays around 8.7 W for 25 seconds (t = 60-85), and drops to and stays around 5 W thereafter (t = 85-120); Impedance decreases from 270 to 240 Ohms (t = 0-120). |
| S2/E6 | Rna/a = 20:100 (seconds): Temperature increases from BT to 50 C. (t = 0-80), and jumps to and stays at 60 C. thereafter (t = 80-120); Power increases from 0 to 8.5 W (t = 0-50), stays around 8.5 W for 28 seconds (t = 50-78), and drops to and stays around 3-5 W thereafter (t = 78-120); Impedance decreases from 280 to 260 Ohms (t = 0-120). |
| S3/E1 | Rna/a = 5:115 (seconds): Temperature increases from BT to 60 C. (t = 0-25), and stays around 60 C. thereafter (t = 25-120); Power increases from 0 to 5 W (t = 0-30), and drops to 4.1 W thereafter (t = 30-120); Impedance decreases from 305 to 250 Ohms (t = 0-120). |
| S3/E2 | Rna/a = 5:115 (seconds): Temperature increases from BT to 60 C. (t = 0-20), and stays around 60 C. thereafter (t = 20-120); Power increases from 0 to 4 W (t = 0-20), and drops to 3.5 W thereafter (t = 20-120); Impedance decreases from 300 to 280 Ohms (t = 0-120). |
| S3/E3 | Rna/a = 20:100 (seconds): Temperature increases from BT to 45 C. (t = 0-20), and stays around 45-47 C. thereafter (t = 20-120); Power increases from 0 to 8.7 W (t = 0-20), and stays around 8.5-8.7 W thereafter (t = 20-120); Impedance decreases from 290 to 250 Ohms (t = 0-120). |
| S3/E4 | Rna/a = 9:111 (seconds): Temperature increases from BT to 54 C. (t = 0-50), and stays around 54 C. thereafter (t = 50-120); Power increases from 0 to 8.5 W (t = 0-120); Impedance decreases from 300 to 290 Ohms (t = 0-120). |
| S3/E5 | Rna/a = 10:110 (seconds): Temperature increases from BT to 53 C. (t = 0-28), and stays around 50-53 C. thereafter (t = 28-120); Power increases from 0 to 8.5 W (t = 0-42), and stays around 8.5 W thereafter (t = 42-120); Impedance decreases from 290 to 260 Ohms (t = 0-120). |
| S3/E6 | Rna/a = 8:112 (seconds): Temperature increases from BT to 60 C. (t = 0-70), and stays around 60 C. thereafter (t = 70-120); Power increases from 0 to 8.5 W (t = 0-78), and drops to 7 W thereafter (t = 78-120); Impedance decreases from 275 to 250 Ohms (t = 0-120) |

Example 3: ED Patient #3

Similar to patient #1, the entire treatment protocol for patient #3 includes three sessions, as summarized in the Table below.

| Session #/<br>Electrode #<br>(S#/E#) | Protocol for Patient #3 |
|---|---|
| S2/E1 | Rna/a = 5:115 (seconds): Temperature increases from BT to 60 C. (t = 0-23), and stays around 60 C. thereafter (t = 23-120); Power increases from 0 to 6.5 W (t = 0-30), and drops to 2.4 W thereafter (t = 30-120); Impedance decreases from 280 to 265 Ohms (t = 0-120). |
| S2/E2 | Rna/a = 9:111 (seconds): Temperature increases from BT to 57 C. (t = 0-40), and stays around 57 C. thereafter (t = 40-120); Power increases from 0 to 8.7 W (t = 0-40), and stays around 8.7 W thereafter (t = 40-120); Impedance decreases from 280 to 260 Ohms (t = 0-120). |
| S2/E3 | Rna/a = 7:113 (seconds): Temperature increases from BT to 60 C. (t = 0-45), and stays around 60 C. thereafter (t = 45-120); Power increases from 0 to 8.5 W (t = 0-55), and drops to 5.5 W thereafter (t = 55-120); Impedance decreases from 295 to 250 Ohms (t = 0-120). |

-continued

| Session #/ Electrode # (S#/E#) | Protocol for Patient #3 |
|---|---|
| S2/E4 | Rna/a = 12:108 (seconds): Temperature increases from BT to 60 C. (t = 0-120); Power increases from 0 to 8.7 W (t = 0-45), and stays around 8.7 W thereafter (t = 45-120); Impedance decreases from 300 to 255 Ohms (t = 0-120). |
| S2/E5 | Rna/a = 8:112 (seconds): Temperature increases from BT to 60 C. (t = 0-30), and stays around 60 C. thereafter (t = 30-120); Power increases from 0 to 5.5 W (t = 0-25), and drops to 2.5 W thereafter (t = 25-120); Impedance increases from 250 to 295 Ohms (t = 0-120). |
| S2/E6 | Rna/a = 19:101 (seconds): Temperature increases from BT to 45 C. (t = 0-19), and stays around 45 C. thereafter (t = 19-120); Power increases from 0 to 8.4 W (t = 0-45), and stays around 8.4 W thereafter (t = 45-120); Impedance decreases from 280 to 270 Ohms (t = 0-120). |
| S3/E1 | Rna/a = 10:110 (seconds): Temperature increases from BT to 60 C. (t = 0-100), and stays around 60 C. thereafter (t = 100-120); Power increases from 0 to 8.5 W (t = 0-65), and drops to 8.3-8.5 W thereafter (t = 65-120); Impedance decreases from 280 to 270 Ohms (t = 0-120). |
| S3/E2 | Rna/a = 6:114 (seconds): Temperature increases from BT to 60 C. (t = 0-30), and stays around 60 C. thereafter (t = 30-120); Power increases from 0 to 5.5 W (t = 0-60), and drops to 4.1 W thereafter (t = 60-120); Impedance decreases from 250 to 205 Ohms (t = 0-120). |
| S3/E3 | Rna/a = 10:110 (seconds): Temperature increases from BT to 60 C. (t = 0-82), and stays around 60 C. thereafter (t = 82-120); Power increases from 0 to 6.7 W (t = 0-80), and drops to 5 W thereafter (t = 80-120); Impedance decreases from 275 to 245 Ohms (t = 0-120). |
| S3/E4 | Rna/a = 7:113 (seconds): Temperature increases from BT to 60 C. (t = 0-55), and stays around 60 C. thereafter (t = 55-120); Power increases from 0 to 6.8 W (t = 0-58), and drops to 5 W thereafter (t = 58-120); Impedance decreases from 290 to 255 Ohms (t = 0-120). |
| S3/E5 | Rna/a = 5:115 (seconds): Temperature increases from BT to 60 C. (t = 0-30), and stays around 60 C. thereafter (t = 30-120); Power increases from 0 to 5 W (t = 0-70), and drops to 4 W thereafter (t = 70-120); Impedance decreases from 295 to 255 Ohms (t = 0-120). |
| S3/E6 | Rna/a = 4:116 (seconds): Temperature increases from BT to 60 C. (t = 0-18), and stays around 60 C. thereafter (t = 18-120); Power increases from 0 to 3 W (t = 0-75), and stays around 3 W thereafter (t = 75-120); Impedance decreases from 210 to 200 Ohms (t = 0-120). |
| S4/E2 | Rna/a = 18:102 (seconds): Temperature increases from BT to 49 C. (t = 0-30), and stays around 47-49 C. thereafter (t = 30-120); Power increases from 0 to 9 W (t = 0-30), and drops to 8.5 W thereafter (t = 30-120); Impedance decreases from 265 to 260 Ohms (t = 0-120). |
| S4/E3 | Rna/a = 15:105 (seconds): Temperature increases from BT to 50 C. (t = 0-40), and stays around 49-50 C. thereafter (t = 40-120); Power increases from 0 to 8.6 W (t = 0-40), and stays around 8.6 W thereafter (t = 40-120); Impedance decreases from 275 to 260 Ohms (t = 0-120). |
| S4/E4 | Rna/a = 11:109 (seconds): Temperature increases from BT to 58 C. (t = 0-120); Power increases from 0 to 8.5 W (t = 0-90), and stays around 8.5 W thereafter (t = 90-120); Impedance decreases from 310 to 285 Ohms (t = 0-120). |
| S4/E5 | Rna/a = 13:107 (seconds): Temperature increases from BT to 57 C. (t = 0-65), and stays around 57 C. thereafter (t = 65-120); Power increases from 0 to 8.5 W (t = 0-60), and stays around 8.5 W thereafter (t = 60-120); Impedance decreases from 300 to 270 Ohms (t = 0-120). |
| S4/E6 | Rna/a = 16:104 (seconds): Temperature increases from BT to 50 C. (t = 0-40), and stays around 50 C. thereafter (t = 40-120); Power increases from 0 to 8.6 W (t = 0-40), and stays around 8.6 W thereafter (t = 40-120); Impedance decreases from 285 to 275 Ohms (t = 0-120). |

Example 4: ED Patient #4

Similar to patient #1, the entire treatment protocol for patient #4 includes one session, as summarized in the Table below.

| Session #/ Electrode # (S#/E#) | Protocol for Patient #4 |
|---|---|
| S1/E1 | Rna/a = 15:105 (seconds): Temperature increases from BT to 59 C. (t = 0-30), and stays around 59 C. thereafter (t = 30-120); Power increases from 0 to 5.8 W (t = 0-38), and drops to 3.5 W thereafter (t = 38-120); Impedance decreases from 240 to 220 Ohms (t = 0-120). |

| Session #/<br>Electrode #<br>(S#/E#) | Protocol for Patient #4 |
|---|---|
| S1/E2 | Rna/a = 17:103 (seconds): Temperature increases from BT to 50 C. (t = 0-35), and stays around 50 C. thereafter (t = 35-120); Power increases from 0 to 8.6 W (t = 0-70), and stays around 8.6 W thereafter (t = 70-120); Impedance decreases from 220 to 205 Ohms (t = 0-120). |
| S1/E3 | Rna/a = 10:110 (seconds): Temperature increases from BT to 51 C. (t = 0-50), and stays around 51 C. thereafter (t = 50-120); Power increases from 0 to 8.3 W (t = 0-80), and stays around 8.3 W thereafter (t = 80-120); Impedance decreases from 220 to 210 Ohms (t = 0-120). |
| S1/E4 | Rna/a = 5:115 (seconds): Temperature increases from BT to 60 C. (t = 0-30), and stays around 60 C. thereafter (t = 30-120); Power increases from 0 to 5 W (t = 0-70), and drops to 4 W thereafter (t = 70-120); Impedance decreases from 295 to 255 Ohms (t = 0-120). |
| S1/E5 | Rna/a = 7:113 (seconds): Temperature increases from BT to 58 C. (t = 0-60), and stays around 58 C. thereafter (t = 60-120); Power increases from 0 to 8.2 W (t = 0-90), and remains about 8.2 W thereafter (t = 90-120); Impedance decreases from 215 to 200 Ohms (t = 0-120). |
| S1/E6 | Rna/a = 5:115 (seconds): Temperature increases from BT to 60 C. (t = 0-50), and stays around 60 C. thereafter (t = 50-120); Power increases from 0 to 4.8 W (t = 0-38), and drops to 4 W thereafter (t = 38-120), Impedance decreases from 220 to 205 Ohms (t = 0-120). |

Example 5: ED Patient #5

Similar to patient #1, the entire treatment protocol for patient #5 includes two sessions, as summarized in the Table below.

| Session #/<br>Electrode #<br>(S#/E#) | Protocol for Patient #5 |
|---|---|
| S1/E1 | Rna/a = 12:108 (seconds): Temperature increases from BT to 56 C. (t = 0-120); Power increases from 0 to 8.4 W (t = 0-70), and stays around 8.4 W thereafter (t = 70-120); Impedance decreases from 205 to 200 Ohms (t = 0-120). |
| S1/E2 | Rna/a = 20:100 (seconds): Temperature increases from BT to 45 C. (t = 0-20), and stays around 45-46 C. thereafter (t = 20-120); Power increases from 0 to 9 W (t = 0-30), and drops to 8.5 W thereafter (t = 30-120); Impedance decreases from 210 to 200 Ohms (t = 0-120). |
| S1/E3 | Rna/a = 19:101 (seconds): Temperature increases from BT to 45 C. (t = 0-19), and stays around 45-46 C. thereafter (t = 19-120); Power increases from 0 to 8.5 W (t = 0-50), and stays around 8.5 W thereafter (t = 50-120); Impedance decreases from 210 to 200 Ohms (t = 0-120). |
| S1/E4 | Rna/a = 15:105 (seconds): Temperature increases from BT to 49 C. (t = 0-50), and stays around 49 C. thereafter (t = 50-120); Power increases from 0 to 8.4 W (t = 0-70) and stays around 8.4 W thereafter (t = 70-120); Impedance decreases from 230 to 205 Ohms (t = 0-120). |
| S1/E5 | Rna/a = 17:103 (seconds): Temperature increases from BT to 52 C. (t = 0-60), and stays around 52 C. thereafter (t = 60-120); Power increases from 0 to 8.3 W (t = 0-85), and stays around 8.3 W thereafter (t = 85-120); Impedance decreases from 245 to 215 Ohms (t = 0-120). |
| S1/E6 | Rna/a = 16:104 (seconds): Temperature increases from BT to 50 C. (t = 0-40), and stays around 50 C. thereafter (t = 40-120); Power increases from 0 to 8 W (t = 0-120); Impedance decreases from 295 to 255 Ohms (t = 0-120). |
| S2/E1 | Rna/a = 9:111 (seconds): Temperature increases from BT to 58 C. (t = 0-60), and stays around 58 C. thereafter (t = 60-120); Power increases from 0 to 6.4 W (t = 0-90), and stays around 6.4 W thereafter (t = 90-120); Impedance decreases from 295 to 255 Ohms (t = 0-120). |
| S2/E2 | Rna/a = 18:102 (seconds): Temperature increases from BT to 50 C. (t = 0-40), and stays around 50 C. thereafter (t = 40-120); Power increases from 0 to 8.5 W (t = 0-55), and stays around 8.5 W thereafter (t = 55-120); Impedance decreases from 215 to 200 Ohms (t = 0-120). |
| S2/E4 | Rna/a = 12:108 (seconds): Temperature increases from BT to 50 C. (t = 0-50), and stays around 50 C. thereafter (t = 50-120); Power increases from 0 to 8.5 W (t = 0-50), and stays around 8.5 W thereafter (t = 50-120); Impedance decreases from 210 to 200 Ohms (t = 0-120). |

| Session #/<br>Electrode #<br>(S#/E#) | Protocol for Patient #5 |
|---|---|
| S2/E5 | Rna/a = 5:115 (seconds): Temperature increases from BT to 60 C. (t = 0-40), and stays around 60 C. thereafter (t = 40-120); Power increases from 0 to 5 W (t = 0-40), and drops to 4 W thereafter (t = 40-120); Impedance decreases from 220 to 205 Ohms (t = 0-120). |
| S2/E6 | Rna/a = 30:90 (seconds): Temperature increases from BT to 48 C. (t = 0-80), and jumps to 60 C. thereafter (t = 80-120), Power increases from 0 to 8.5 W (t = 0-55), stays around 8.5 W(t = 55-80), and drops to 4.1 W thereafter (t = 80-120); Impedance decreases from 275 to 255 Ohms (t = 0-120). |

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A method of treating or alleviating erectile dysfunction in a patient comprising (1) placing multiple electrodes of a catheter apparatus within a segment of an internal iliac artery of the patient and against a blood vessel wall of the internal iliac artery by percutaneous transluminal intravascular access; (2) adhering a surface electrode on an external surface such as skin of the patient; and (3) releasing radiofrequency energy through at least one of the multiple electrodes to nearby tissues, so as to increase the temperature of the nearby tissues and induce a thermal alteration of the nearby tissues; wherein the catheter apparatus comprises: an elongated shaft having a proximal portion and a distal portion; a carrier carrying at least one therapeutic assembly, wherein the carrier is located at, or proximate to, the distal portion of the elongated shaft, and wherein the at least one therapeutic assembly comprises the multiple electrodes for intravascular treatment; wherein the carrier is configured to vary between a delivery configuration and a deployed configuration: wherein the distal portion of the shaft is configured for intravascular delivery of the carrier: wherein the carrier comprises m (m is at least two) right-handed wire helixes and n (n is at least two) left-handed wire helixes that are plainly or bi-axially woven into each other: wherein the carrier comprises at least one interstice that is defined by four wire helix segments from two of the immediately adjacent at least two right-handed wire helixes and two of the immediately adjacent at least two left-handed wire helixes that are plainly or bi-axially woven into each other; wherein said at least one therapeutic assembly wraps around at least one of said four wire helix segments to stabilize said at least one interstice, to maintain structural integrity of the carrier, and to prevent tangling of the m right-handed wire helixes and the n left-handed wire helixes, when the carrier is being distorted intravascularly, wherein at least two of the m right-handed wire helixes and at least two of the n left-handed wire helixes are made from two single wires each having a first portion of right-handed wire helix and a second portion of left-handed wire helix by folding or bending a point of the single wire between the first portion and the second portion at an angle of from about 160 to 180 degree; wherein the catheter apparatus further comprises a multi-lumen bundler, wherein the multi-lumen bundler has a cylinder body, and a number of lumens pass axially through the cylinder body along the longitudinal axis of the cylinder body; wherein said two single wires each having a first portion of right-handed wire helix and a second portion of left-handed wire helix are inserted into, and pass through, a same lumen selected from said a number of lumens; and wherein the first portion of right-handed wire helix of each of said two single wires is inserted into and passes through one of said a number of lumens, the second portion of left-handed wire helix of said each one of said two single wires is inserted into and passes through another of said number of lumens, and said each one of said two single wires is permanently glued and fixed to the multi-lumen bundler with a liquid adhesive material filled into or dropped into the lumens and solidified thereafter.

2. The method according to claim 1, further comprising: adjusting or changing the adhesion position of the surface electrode on the back or butt of the patient to vary the impedance between the surface electrode and a given electrode of the multiple electrodes placed within the internal iliac artery until the impedance falls within the range of 200-320 Ohms, before step (2).

3. The method according to claim 1, wherein the radiofrequency energy is released at a level of no more than 9 W (joule per second) to prevent spasm of the patient.

4. The method according to claim 1, wherein the radiofrequency energy is released with a temperature threshold setting of 60° C.to ensure that collagen does not denature, tissue does not shrink, and cell wall does not break, in the nearby tissue.

5. The method according to claim 1, wherein the radiofrequency energy is released through an alternating current of 460-470 KHz between the surface electrode and a given electrode of the multiple electrodes placed within the internal iliac artery.

6. The method according to claim 5, wherein the radiofrequency energy is released through an alternating current of 465 KHz between the surface electrode and a given electrode of the multiple electrodes placed within the internal iliac artery.

7. The method according to claim 1, wherein the segment starts from the junction of the internal iliac artery and the common iliac artery.

8. The method according to claim 1, wherein said thermal alteration comprises a non-ablative thermal alteration with a temperature of <45° C.and an ablative thermal alteration with a temperature of >45° C.;

wherein a time period for the non-ablative thermal alteration during step (3) is defined as Tna, a time period for the ablative thermal alteration during step (3) is defined as Ta, and the ratio between the two is defined as Rna/a; wherein Rna/a values during step (3) are in the range of from 4:116 to 72:48; and wherein a nocturnal penile tumescence (NPT) test for the patient using standard Rigiscan Campbell Urology 2006 after step (3) demonstrates a significant increase of Erection Time Length and Erection Frequency; and wherein the radiofrequency energy is released for a continuous period of 60-180 seconds such as 120 seconds for each of the multiple electrodes one by one, which protocol is defined as one session; and wherein step (3) comprises one, two, three, four, or more such sessions that are separately carried out.

9. The method according to claim 8, wherein the thermal alteration produces a lesion with a depth of 5-8 mm or 5.9-6.9 mm such as about 6.4 mm in the nearby tissues.

10. The method according to claim 8, wherein step (3) consists of two sessions that are separately carried out on a patient using six electrodes of the multiple electrodes in each session, wherein the Rna/a values of the six electrodes in a first session comprises 10:110, 25:95, 10:110, and 15:105; wherein the Rna/a values of the six electrodes in a second session comprises 10:110, 10:110, 10:110, 10:110, 5:115 and 15:105; and wherein NPT test for the patient using standard Rigiscan Campbell Urology 2006 demonstrates an increase of Erection Time Length from 6 minutes to 43 minutes, and an increase of Erection Frequency from 1 Time to 3 Times during a 10-hour monitoring time length.

11. The method according to claim 8, wherein the Rna/a within a session for a patient comprises 20:100, 25:95, 30:90, 72:48, or any combination thereof.

12. The method according to claim 10, wherein the six electrodes are configured to create interrupted spiral but full circumferential lesions on internal wall of said segment of the internal iliac artery of the patient.

13. The method according to claim 1, wherein said at least one therapeutic assembly wraps around only one of said four wire helix segments to stabilize the at least one interstice.

14. The method according to claim 13, wherein said at least one therapeutic assembly includes two terminal bodies and a main body positioned between the two terminal bodies; and wherein cross-sectional area of the main body along a plane perpendicular to the elongation direction of a wire segment being wrapped around is larger than cross-sectional areas of the terminal bodies along a plane perpendicular to the elongation direction of the wire segment being wrapped around, which are larger than a cross-sectional area of the wire segment being wrapped around along a plane perpendicular to the elongation direction of the wire segment.

15. The method according to claim 14, wherein a length of the wire segment being wrapped around is maintained to be equal to, or longer than, the main body's length along the elongation direction of the wire segment being wrapped around.

16. The method according to claim 14, wherein a length of the wire segment being wrapped around is maintained to be equal to, or longer than, the main body's length combined with length of one of the two terminal bodies, or total length of the two terminal bodies, along the elongation direction of the wire segment being wrapped around.

17. The method according to claim 14, wherein at least one of the two terminal bodies and the main body includes (1) one or more grooves for accommodating or guiding one or more wire helixes that slide(s) over the wire segment around which the therapeutic assembly wraps; and/or (2) one, two or more protrusions, wherein the gap(s) between the protrusion(s) and the wire segment around which the therapeutic assembly wraps, and the gap(s) between said protrusion(s) themselves, is(are) configured for accommodating or guiding one or more wire helixes that slide(s) over the wire segment around which the therapeutic assembly wraps.

\* \* \* \* \*